United States Patent
Lee et al.

(10) Patent No.: US 10,898,894 B2
(45) Date of Patent: Jan. 26, 2021

(54) MICROFLUIDIC DIAGNOSTIC ASSEMBLY

(71) Applicants: New Jersey Institute of Technology, Newark, NJ (US); Hackensack University Medical Center, Hackensack, NJ (US)

(72) Inventors: Eon Soo Lee, Hackensack, NJ (US); Bharath Babu Nunna, Randolph, NJ (US); K. Stephen Suh, Hackensack, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 208 days.

(21) Appl. No.: 16/312,091

(22) PCT Filed: Jun. 21, 2017

(86) PCT No.: PCT/US2017/038554
§ 371 (c)(1),
(2) Date: Dec. 20, 2018

(87) PCT Pub. No.: WO2017/223205
PCT Pub. Date: Dec. 28, 2017

(65) Prior Publication Data
US 2019/0201892 A1    Jul. 4, 2019

Related U.S. Application Data

(60) Provisional application No. 62/353,404, filed on Jun. 22, 2016.

(51) Int. Cl.
*G01N 21/00* (2006.01)
*B01L 3/00* (2006.01)
*G01N 33/543* (2006.01)

(52) U.S. Cl.
CPC ........ *B01L 3/502707* (2013.01); *G01N 21/00* (2013.01); *G01N 33/54366* (2013.01);
(Continued)

(58) Field of Classification Search
CPC ....... B01L 3/502707; B01L 2300/0645; B01L 2300/0816; B01L 2300/0883; B01L 2300/0887; G01N 21/00; G01N 33/54366
See application file for complete search history.

(56) References Cited

U.S. PATENT DOCUMENTS

2011/0247934 A1* 10/2011 Wang ................ B01L 3/502792
204/450

* cited by examiner

*Primary Examiner* — Jennifer Wecker
*Assistant Examiner* — Michael Paul Shimek
(74) *Attorney, Agent, or Firm* — McCarter & English, LLP

(57) ABSTRACT

Improved diagnostic assemblies are provided. More particularly, the present disclosure provides improved and highly advantageous chip based diagnostic assemblies configured to detect human diseases (e.g., cancer) and/or pathogens, and related methods of use. In exemplary embodiments, the present disclosure provides for consumable micro- or nano-fluidic chip based diagnostic assemblies having visual biosensors, with the diagnostic assemblies using continuous flow-based micro- or nano-fluidic channels and antibody-based immuno-complex designs. In certain embodiments, the diagnostic assembly includes a self-sustainable and operable chip (e.g., thumb-sized chip) that is configured to be deployed as a single use consumable with a direct all-or-none readout as an output to satisfy a point of screening method to screen a population.

20 Claims, 25 Drawing Sheets

(52) U.S. Cl.
CPC ............... *B01L 2300/0645* (2013.01); *B01L 2300/0816* (2013.01); *B01L 2300/0883* (2013.01); *B01L 2300/0887* (2013.01)

MICROFLUIDIC DIAGNOSTIC ASSEMBLY

CROSS-REFERENCE TO RELATED APPLICATIONS

This application claims the benefit of U.S. Provisional application entitled "MICROFLUIDIC DIAGNOSTIC ASSEMBLY," which was filed on Jun. 22, 2016, and assigned Ser. No. 62/353,404, the contents of which are herein incorporated by reference in its entirety.

FIELD OF THE DISCLOSURE

The present disclosure relates to diagnostic assemblies and, more particularly, to chip based diagnostic assemblies configured to detect human diseases (e.g., cancer) and/or pathogens.

BACKGROUND OF THE DISCLOSURE

In general, human diseases can be diagnosed by multiple diagnostic methods. For example, diagnostics on biofluids, especially from serum samples, have been used typically on platforms such as "enzyme-linked immunosorbent assay" or "ELISA" in reference laboratories and pathology departments worldwide, and the use of this immunoassay technology is more than four decades old. General statistics show that some sources of the biomaterials for ELISA platforms are serum (near 70%) and the rest is generally composed of plasma, cultured cells, whole blood and cell lysates. Preparation of serum from whole blood generally is a required step for typical clinical ELISA analyses.

ELISA that conforms to Clinical Laboratory Improvement Amendments ("CLIA") and formatted for clinical diagnosis is mostly available in kits and the assay reagents are included in kits for convenience. However, the process can be laborious and partly wasteful since the ninety-six wells are often not used at once. In addition, various detection chemistries are available for ELISA, including Horse Radish Peroxidase ("HRP")-colorimetric (near 90%), and the rest that are generally represented by Alkaline Phosphatase ("AP")-colorimetric and HRP-chemiluminescent.

In general, many clinical and reference laboratories do not use automated ELISA and less than 15% are using partial automation due to the high cost of the automated ELISA robotic platform. As such, the majority of formats are locked in with the ninety-six well plate, the ELISA plate washers and readers for most clinical pathology and reference laboratories. This general ELISA format that dominates clinic and related CLIA laboratory methods can pose important challenges. For example, such traditional methods can: (i) lack sensitivity for low abundant biomarkers, (ii) require large biomaterial and reagent consumption, (iii) include high costs associated with analyses, and/or (iv) be unable to be deployed for mass population screenings for a given disease. Furthermore, the implementation of proteomics and a generally widespread requirement of multiplexing analytical needs can put pressure to develop the next generation immunoassay format that can alleviate multiple problems with assay performance and costs and attempt to overcome operational drawbacks in various clinical and public settings.

In general, cancer is a group of diseases characterized by uncontrolled growth and spread of aggressive cancer cells to other parts of the body and can result in death. Currently, cancer causes deaths worldwide with over 12.6 million new cancer cases diagnosed annually, and the disease impacts around 13% of deaths worldwide. Despite advancements in biomedical technology, the World Health Organization estimates 12 million cancer related deaths by 2030 without significant prevention measures adopted for population screening and during routine clinical visits.

Early detection of cancer during its onset at an early stage is an important prevention measure and this generally is the stage where the disease is most treatable. Such prevention measures can reduce healthcare costs and improve the quality of life for patients. To achieve early detection of specific cancer types, highly sensitive and specific sets of biomarkers may be required. These cancer specific and early stage sensitive biomarkers can be substances that are expressed on cancer cells or created by the body's immune system in response to cancer cells. These types of biomarkers can be found in tissue, blood, or urine, and the detection of these specific cancer biomarkers in higher-than-normal amounts in the body may signify the presence of cancer.

Further efforts include identifying which specific cells express the marker and which do not enable the distinction between cancerous cells and healthy cells. Once a tumor has been located and associated with a marker, that marker can be used to monitor treatment and possible recurrence, indicate the likelihood of progression, and assist with a prognosis. Depending upon the patient and the cancer, post-treatment follow-up tests for a particular marker may continue for life, as frequently as every two to three months.

Ovarian cancer ("OVC") ranks as the fifth most common cancer in women and has the highest mortality rate among gynecologic malignancies. Although the 5-year survival rate of OVC is around 90% when detected in its early stages (I/II), the long-term survival rate is as low as 15% for advanced stage patients. Conventional surgery with chemotherapy can cure about 90% of patients if diagnosed in stage I. However, over 70% of OVC patients at the time of diagnosis are at advanced stages because the disease is asymptomatic. The disease spreads quickly because OVC, unlike other solid tumors, starts to metastasize at stage II and these OVC cells migrate efficiently to neighboring tissues, especially within the peritoneum cavity. Nearly 80% of OVC patients experience a relapse after first-line chemotherapy, therefore requiring subsequent therapies. The costs of OVC patient care is estimated at over S2 billion annually in the U.S. alone, and these costs are expected to increase 45% from 2010 to 2020 due to an aging population. Thus, early detection of OVC is an important component to reduce healthcare cost and decrease mortality rate in the female population.

Recently, two proteins have been approved as OVC biomarkers. One of the commonly used biomarkers is CA-125. It is noted that while CA-125 is elevated in 80-90% of advanced stage OVC patients, 47% of early-stage patients present normal CA-125 values. In addition, its high false-positive rate can be implicated in elevated levels in benign conditions, pregnancy, pelvic inflammation and endometriosis. HE4, although it is less elevated in benign conditions and presented as a better early stage biomarker, has been approved by the U.S. FDA but not for screening purposes.

Some exemplary detection assemblies and related methods, devices and accessories or the like are described and disclosed in U.S. Pat. Nos. 8,208,138 and 8,071,057, and U.S. Patent Pub. No. 2001/0036644, the entire contents of each being hereby incorporated by reference in their entireties.

Thus, an interest exists for improved diagnostic assemblies, and related methods of use. These and other inefficiencies and opportunities for improvement are addressed and/or overcome by the assemblies, systems and methods of the present disclosure.

SUMMARY OF THE DISCLOSURE

The present disclosure provides improved diagnostic assemblies. More particularly, the present disclosure provides advantageous chip based diagnostic assemblies configured to detect human diseases (e.g., cancer) and/or pathogens.

In exemplary embodiments, the present disclosure provides for consumable micro- or nano-fluidic chip based diagnostic assemblies having visual biosensors, with the diagnostic assemblies using continuous flow-based micro- or nano-fluidic channels and antibody-based immuno-complex designs.

In certain embodiments, the diagnostic assembly includes a self-sustainable and operable chip (e.g., thumb-sized chip) that is configured to be deployed as a single use consumable with a direct all-or-none readout as an output to satisfy a point of screening method to screen a population. The diagnostic assembly can be a point-of-care diagnostic depending on the antigen for detection and the situation that governs immediate healthcare needs.

The present disclosure provides for a diagnostic assembly including a channel layer having a top surface and a bottom surface, the channel layer including a channel that extends from the bottom surface toward the top surface, with the channel ending at a point between the top and bottom surfaces; an insulation layer having a top surface and a bottom surface, the top surface of the insulation layer having a coated area, with the top surface of the insulation layer positioned under the bottom surface of the channel layer to seal the channel, with the coated area positioned under the channel; a circuit layer having a top surface and a bottom surface, the top surface of the circuit layer positioned under the bottom surface of the insulation layer and under the coated area; wherein after a fluid flow is introduced to the channel, the circuit layer is configured to generate signals based on interactions of the fluid flow with the coated area.

The present disclosure also provides for a diagnostic assembly wherein the channel layer includes polydimethylsiloxane; wherein the channel includes a shape selected from the group consisting of serpentine, spiral, straight and curved; and wherein the channel is hydrophilic.

The present disclosure also provides for a diagnostic assembly wherein the channel includes a width from about 200 µm to about 300 µm and includes a depth from about 60 µm to about 100 µm. The present disclosure also provides for a diagnostic assembly wherein the fluid flow includes blood and the coated area includes antibodies or antigens; and wherein the channel extends from an inlet well to an outlet well.

The present disclosure also provides for a diagnostic assembly wherein the shape of the coated area substantially matches the shape of the channel; and wherein the shape of the circuit layer substantially matches the shape of the channel.

The present disclosure also provides for a diagnostic assembly wherein the circuit layer is mounted to a polymeric base member, the polymeric base member having a plurality of lights mounted thereto, the plurality of lights configured to illuminate to display the signals.

The present disclosure also provides for a diagnostic assembly including a channel layer having a top surface and a bottom surface, the channel layer including a channel that extends from the bottom surface toward the top surface, with the channel ending at a point between the top and bottom surfaces; an insulation layer having a top surface and a bottom surface, the top surface of the insulation layer having a coated area, with the top surface of the insulation layer positioned under the bottom surface of the channel layer to seal the channel, with the coated area positioned under the channel; a circuit layer having a top surface and a bottom surface, the top surface of the circuit layer positioned under the bottom surface of the insulation layer and under the coated area; a control panel layer mounted to the bottom surface of the circuit layer, the control panel layer including a signal receiver, a signal amplifier and a signal processor; wherein after a fluid flow is introduced to the channel, the circuit layer is configured to generate signals based on interactions of the fluid flow with the coated area; wherein the control panel layer is configured to process and receive the signals via the signal receiver and the signal amplifier, and the signal processor is configured to process the signals and to visually display the signals.

The present disclosure also provides for a diagnostic assembly further including a plurality of lights mounted to the control panel layer, the plurality of lights configured to illuminate to display the signals.

The present disclosure also provides for a diagnostic assembly wherein the control panel layer further includes an electrical oscillation generator; and wherein the circuit layer is configured to generate signals based on frequency response variations to electrical oscillation from the channel.

The present disclosure also provides for a diagnostic assembly wherein the circuit layer is configured to generate signals based on temperature variations in the channel. The present disclosure also provides for a diagnostic assembly wherein the channel has a cross-sectional shape selected from the group consisting of rectangular, square, eclipse-shaped, circular, rhombus, trapezoid and polygonal.

The present disclosure also provides for a diagnostic assembly wherein the fluid flow includes blood and the coated area includes antibodies or antigens; and wherein the channel extends from an inlet well to an outlet well.

The present disclosure also provides for a diagnostic assembly wherein the shape of the coated area substantially matches the shape of the channel; and wherein the shape of the circuit layer substantially matches the shape of the channel.

The present disclosure also provides for a diagnostic assembly including a channel layer having a top surface and a bottom surface, the channel layer including a channel that extends from the bottom surface toward the top surface, with the channel ending at a point between the top and bottom surfaces; an insulation layer having a top surface and a bottom surface, the top surface of the insulation layer having a coated area, with the top surface of the insulation layer positioned under the bottom surface of the channel layer to seal the channel, with the coated area positioned under the channel; a first circuit layer and a second circuit layer, with a dielectric material positioned between the first and second circuit layers, a top surface of the first circuit layer positioned under the bottom surface of the insulation layer and under the coated area, and a bottom surface of the second circuit layer mounted to a base member; a control panel layer mounted to a bottom surface of the base member, the control panel layer including a signal receiver, a signal amplifier and a signal processor; wherein after a fluid flow is introduced to the channel, the first and second circuit layers are configured to generate signals based on interactions of the fluid flow with the coated area. The present disclosure also provides for a diagnostic assembly wherein the control panel layer is configured to process and receive the signals via the signal receiver and the signal amplifier, and the signal processor is configured to process the signals and to visually display the signals.

The present disclosure also provides for a diagnostic assembly further including a plurality of lights mounted to the control panel layer, the plurality of lights configured to illuminate to display the signals.

The present disclosure also provides for a diagnostic assembly wherein the first and second circuit layers are configured to generate signals based on voltage variations in the channel.

The present disclosure also provides for a diagnostic assembly wherein the channel layer includes polydimethylsiloxane; wherein the channel includes a shape selected from the group consisting of serpentine, spiral, straight and curved; wherein the channel is hydrophilic; and wherein the channel has a cross-sectional shape selected from the group consisting of rectangular, square, eclipse-shaped, circular, rhombus, trapezoid and polygonal.

The present disclosure also provides for a diagnostic assembly wherein the fluid flow includes blood and the coated area includes antibodies or antigens; and wherein the channel extends from an inlet well to an outlet well.

The present disclosure also provides for a diagnostic assembly wherein the shape of the coated area substantially matches the shape of the channel; and wherein the shapes of the first and second circuit layers substantially match the shape of the channel.

Any combination or permutation of embodiments is envisioned. Additional advantageous features, functions and applications of the disclosed assemblies, systems and methods of the present disclosure will be apparent from the description which follows, particularly when read in conjunction with the appended figures. The references, publications and patents listed in this disclosure are hereby incorporated by reference in their entireties.

BRIEF DESCRIPTION OF THE DRAWINGS

Features and aspects of embodiments are described below with reference to the accompanying drawings, in which elements are not necessarily depicted to scale.

Exemplary embodiments of the present disclosure are further described with reference to the appended figures. It is to be noted that the various features, steps and combinations of features/steps described below and illustrated in the figures can be arranged and organized differently to result in embodiments which are still within the scope of the present disclosure. To assist those of ordinary skill in the art in making and using the disclosed assemblies, systems and methods, reference is made to the appended figures, wherein.

DETAILED DESCRIPTION OF THE DISCLOSURE

Figure 1:
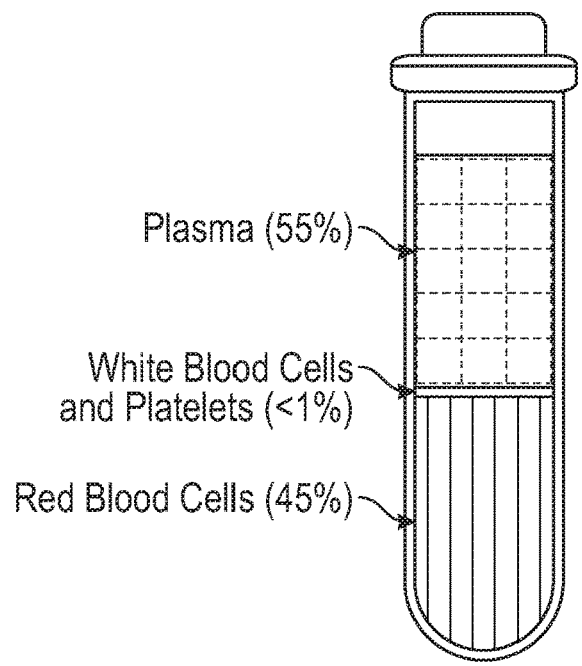
FIG. 1 shows a graphical representation (not to scale) of the composition of blood.

The exemplary embodiments disclosed herein are illustrative of advantageous diagnostic assemblies, and systems of the present disclosure and methods/techniques thereof. It should be understood, however, that the disclosed embodiments are merely exemplary of the present disclosure, which may be embodied in various forms. Therefore, details disclosed herein with reference to exemplary systems/assemblies and associated processes/techniques of assembly and use are not to be interpreted as limiting, but merely as the basis for teaching one skilled in the art how to make and use the advantageous assemblies, systems and methods of the present disclosure.

The present disclosure provides advantageous diagnostic assemblies. More particularly, the present disclosure provides advantageous chip based diagnostic assemblies configured to detect human diseases (e.g., cancer) and/or pathogens, and related methods of use.

In certain embodiments, the present disclosure provides for consumable micro- or nano-fluidic chip based diagnostic assemblies having visual biosensors, with the diagnostic assemblies using continuous flow-based micro- or nano-fluidic channels and antibody-based immuno-complex designs.

In some embodiments, the diagnostic assembly includes a self-sustainable and operable chip (e.g., thumb-sized chip) that is configured to be deployed as a single use consumable with a direct all-or-none readout as an output to satisfy a point of screening method to screen a population.

Exemplary advances in microfluidic technologies can provide better "enzyme-linked immunosorbent assay" or "ELISA" formatting options to use biomaterials in the micro-liter ranges, and digital technologies supporting the format can increase detection sensitivies. An exemplary ELISA can be in a format of a micro- or nano-chip that utilizes a micro- or nano-fluidics structure and utilizes self-sustainable detection technology. Such type of chip can utilize a robust set of biomarkers to maximize sensitivity and integrate exemplary technologies to overcome major obstacles of conventional ELISA formats. Such an exemplary chip (e.g., micro-chip) can be utilized to detect complex human diseases, including cancer, and for carrying out multivariate assays in an extremely user-friendly format, so that the end users can generate metrics for accurate diagnosis, prognosis and treatment efficacy. The robust set of biomarkers that are specific for cancer type can significantly increase sensitivity and specificity, especially for early detection of cancer from the population.

Thus, self-sustainable diagnostic chips (e.g., micro-chips) can be used for both point-of-screening and point-of-care diagnostics tools. Examples of multiplexing of biomarkers can be found in current assay formats, and such assays with a panel with multiple biomarkers have consistently shown to increase accuracy of identifying prospective cancer patients when compared with single biomarker assays.

For use of an exemplary chip, it can have attributes on: (i) a self-sustainable energy in order to start-to-finish the assay by using a micro-battery powered visualization of positive signals, (ii) low costs to be used in settings as a consumable format and disposable, (iii) low operating costs by constructing a chip that can be used by many users (e.g., to an 8th grade education level), (iv) an open system for other entities to add biomarkers or other technologies for improving the use of the chip, (v) an extremely low sample volume by targeting less than 5 ul of whole blood from a finger-prick, and/or (vi) a high throughput assay format in respect to real time for mass screening and during routine clinic visits. To meet such criteria, the present disclosure provides for an exemplary diagnostic micro-chip that utilizes micro-fluidic channels and utilizes validated sets of antibodies and biomarkers. In certain embodiments and without limitation, it is noted that the exemplary diagnostic assembly can be utilized for the early detection of ovarian cancer.

As discussed further below, the present disclosure provides for the designs and configurations of the microfluidic channeling, the precision etching, and fabrication of exemplary chips. In certain embodiments, the present disclosure provides for custom made rabbit anti-peptide polyclonal antibodies against early detection biomarkers Kalikrein-6 ("KLK6"), Kalikrein-7 ("KLK7") and Protease Serine-8/Prostasin ("PRSS8"), positive recombinant protein controls, antigen-antibody binding and optimization and patient serum samples from normal donors and ovarian cancer patients from benign and stage I-IV.

It is noted that an exemplary diagnostic assembly can be utilized for the early detection of ovarian cancer, but the assemblies can be utilized for other cancers and non-cancer disease types. It is further noted that current clinical environments lack a robust set of biomarkers for early detection of cancer and do not utilize detection platforms that are in a microchip format for ease of use by clinicians with minimal training.

Moreover, the need of identifying robust biomarkers for OVC is a clinical unmet need. To address such challenges, the present disclosure identifies the biomarkers KLK6, KLK7 and PRSS8 that can be used alone or in combination with clinical CA125 and HE4 to significantly increase overall sensitivity and specificity in early detection of OVC.

The present disclosure provides for the validation and testing of a microchip based diagnostic assembly.

An exemplary microchip can use anti-peptide antibodies raised against KLK6, KLK7 and PRSS8, and the testing can be done with normal donor samples from females and samples procured during OB/GYN routine clinical visits. Due to customized development of anti-peptide antibodies from the ground up, the three antibodies are highly specific for targets KLK6, KLK7 and PRSS8 in human bio-fluid samples. Preliminary data from Western Analysis indicates that about 0.2 ul of human serum can be used to detect the presence of KLK6, KLK7 and PRSS8. Based on molecular characterizations, these fabricated antibodies against N- and C-termini of KLK6, KLK7 and PRSS8 showed greater than 1000 fold higher specificity and affinity than commercially available antibodies. These three antibodies can be ligated to the micro-channels of the microchip to generate a diagnostic assembly that requires minimal training time.

The present disclosure provides for the role of a biomarkers panel in the form of a micro-fluidic diagnostic chip of a diagnostic assembly (e.g., for cancer detection).

In general, the development of most cancers can require multiple steps that occur over years. The complexity of cancer can require multi-variate assays for accurate diagnosis, prognosis and treatment monitoring. Given the multi-variate and heterogeneous nature of the disease, assays with multiple analytes are expected to increase the sensitivity and specificity for early detection and diagnosis of cancer. However, these multiple analytes/biomarkers should be highly specific and robust across the population in general. As examples, a panel of 6 biomarkers for ovarian cancer and a panel of cancer markers for breast cancer have been reported with high sensitivity and specificity for early detection. For instance, researchers have reported specificity of around 56% for using CA-125 as a marker for the early detection of ovarian cancer (stage I and II). However, when CA-125 is used in conjunction with other biomarkers as a 6-marker panel, the sensitivity and specificity are both improved to 95% each.

Similarly, for oestrogen receptor-positive (ER+) breast cancer, researchers have reported a four-fold improvement in identifying patients with poor prognosis by using a panel of 5 biomarkers as opposed to any one marker alone. These findings are increasingly accepted by the researchers and clinicians and some in the field of diagnostics agree that a panel of biomarkers can be more efficacious at early and accurate detection of cancerous states than any one biomarker alone. In order to implement these multi-marker tests in a clinical setting, an exemplary test system should offer the following attributes, as individually discussed further below: (i) Open system, (ii) Low capital cost, (iii) Low operating costs, (iv) Low sample volume, and (v) High throughput.

Open System:

Some central lab tests running in the reference or pathology laboratories are "closed" systems where new tests can only be added by the system manufacturers as in bulk format and not in incremental format. This means the clinic may have to wait for years to provide better clinical care for patients. Closed systems are typically reliable and cost-effective but they tend to offer limited menus and limit the benefit to the general population and for the patients.

Low Capital Cost:

Some immunoassay diagnostic analyzers/systems are sold as "equipment" or as in "kit" formats. In some cases, hospitals and labs purchase these under a "reagent rental model" and will likely not change the model for years until the cost to benefit ratio mandates the change due to budgetary and efficiency issues. This type of workflow can limit clinical benefits to patients. The cost of the instrument can be amortized over a number of tests expected on an annual/lifetime basis. A high capital cost can directly translate to a higher per test cost. Although in some cases such as infectious disease diagnosis this can be acceptable (since few tests are generally needed for a diagnosis), for a multi-marker cancer panel this cost can rapidly become prohibitive. For instance, an 8 to 10 cancer panel test can easily run up to S100's for the test lab and significantly more for the patient. This can directly translate to increased healthcare costs. In low-resource nations, this unfortunately translates to the inability to run multi-marker tests due to cost constraints.

Low Operating Costs:

Operating costs can accrue from the required maintenance costs and more importantly from the recurring reagent costs. Even the costs of relatively inexpensive reagents such as wash buffers become noticeable when a 50-gallon wash buffer drum is required for a lab-based analyzer.

Low Sample Volume:

Some diagnostic instrument use around 20 to 100 µl of sample per test point typically of serum (for blood based tests). For example, around 250 µl of whole blood per test point. For a 10-plex panel this can translate to at least 2.5 ml sample; which may not be an issue for adults but can become increasingly challenging for pediatric patients. The exemplary microfluidic chip based model of the present disclosure can require a 5 to 10 ul volume or less that can be supplemented from a finger prick amount of blood that is similar to diabetics tests.

High Throuput:

In of itself, rapid test times can be of very little relevance to cancer detection. Unfortunately, throughput can also drive the per test cost since the equipment is "locked" for running a multi-marker test as opposed to running more lucrative single point tests with higher returns for the lab. A high throughput system can effectively lower this cost across test cases and make multi-marker tests more feasible.

Conventional technologies and systems may attempt to address one or more of these capabilities, but there is no single conventional system that delivers these capabilities. The exemplary micro-fluidic diagnostic chips of the diagnostic assemblies of the present disclosure can advantageously address these challenges. The exemplary diagnostic assemblies can specifically target the cost metrics desired and with the inherent benefits of microfluidics can also advantageously deliver on the above requirements.

In exemplary embodiments, disease diagnosis (e.g., cancer diagnosis) is performed on a micro-fluidic chip assembly using a micro-blood sample. The micro-fluidic chip can include a channel layer (e.g., a polydimethylsiloxane or PDMS micro-channel layer) through which the cancer affected patient's blood is flowed through. The microchannel of the channel layer can be designed in such a way that the blood is flowed by its natural capillary force without any external force. Techniques like electro-wetting and plasma oxidation can be applied on the channel of the channel layer to convert it from hydrophobic to hydrophilic. Some well structures can be introduced at the surfaces of the channel layer in order to facilitate blood for mixing and particle (e.g., Erythrocytes—RBC) transportation.

At least portions of the surfaces of the walls of the channel can be treated with antibodies at specified lengths of the channel. As the antibodies which are coated to the surface of the channel are predetermined, the antigens that are bonded to these antibodies are evident. The existence of cancer antigens in the blood sample that is flowed through the micro-channel provides the evidence of cancer. This qualitative approach is helpful to examine the existence of cancer in patient blood.

The computation of bonding formed between antigen and antibody in the specified length of the channel for a known volume of blood sample gives the quantitative results of the cancer diagnosis. The antigen and antibody bonding is captured by applying the principle of a capacitor whose output can be a digital signal. These digital signals can be displayed on a screen for better visualization of the results.

Conventional Well-Type Diagnostic Device—ELISA:

A conventional method in order to diagnose cancer is enzyme-linked immunosorbent assay or ELISA. Antigens from the cancer related blood sample is attached to the surface. A further specific antibody is applied to the surface facilitating to form the bond with antigen. This antibody is linked to an enzyme and in the final step an enzyme substrate is added. Subsequent reaction produces a signal like a substrate color change to indicate the existence of cancer antigens in the blood. ELISA generally needs to be executed in the lab. Some advantages of the cancer diagnosis with the exemplary micro-chips of the present disclosure compared to the conventional method of ELISA can include:

1) The volume of blood considered for diagnosis in the exemplary microchip is in micro-liters which is very minimum, when compared to conventional ELISA methods.
2) The blood sample can be examined instantaneously in the exemplary microfluidic chip, unlike conventional ELISA which has many additional steps involved to attempt to ensure that the blood properties are not disturbed between blood sample collection and actual diagnosis.
3) Due to the compact nature of the exemplary microfluidic chip and its easy operation, this makes this device a personal self-evaluation unit for cancer. But the conventional ELISA should only be performed with a highly skilled and trained technician in a well-established diagnostic center.
4) Since the exemplary microfluidic chip can be manufactured with very low expense when compared to the sophisticated lab set up to perform conventional ELISA, the exemplary cancer diagnosis can become an inexpensive exercise and affordable for many 5) As the exemplary microfluidic chip diagnosis for cancer is an easy process compared to conventional ELISA, the tendency of getting examined for cancer will increase and hence the existence of cancer in patients can be diagnosed in much earlier stages, which will save lives.

Once the cancer diagnosis is performed using an exemplary microfluidic chip, the treatment methods or preventive methods can be programmed in the microfluidic chip so that the patients can know the current situation and act according to requirements.

Though there are prevailing methods like conventional ELISA (Enzyme-linked immunosorbent assay) to identify cancer antigens in blood, it is a very long process incorporating much equipment.

The present disclosure provides for the fabrication of a biochip which can diagnose the cancer antigens in a microvolume of blood sample. Using such advantageous assemblies, one can significantly reduce the time and cost factors involved in the diagnosis of cancer, and importantly the quantity of blood used to diagnose is minimum (e.g., micro volume) when compared to conventional diagnostic methods. Reducing the diagnosis processes to a user-friendly method in the micro-level allows a potential patient to administer self-examination.

As part of designing an exemplary micro-channel of a channel layer, studying the blood flow phenomenon is important. To date, the flow of blood is not completely understood as it gets influenced by various factors of flow conditions existing in the micro-channel environment such as surface tension and capillary forces.

Though blood plasma is a Newtonian fluid, the red blood cells (RBCs-erythrocytes), which are deformable in nature, can change the characteristic of blood to a non-Newtonian fluid. One focus of the present disclosure is to understand the non-Newtonian blood flow phenomenon with varied microchannel cross sections and surface treatments. Studies can be conducted on the RBCs flow, since RBCs in the blood is a key factor which impacts the flow and flow rate of blood.

The study on blood coagulation is another important element which can be considered for channel design. Considering the blood coagulation, the blood flow in a channel is time dependent. Through this research, the diagnosis process can be done before the blood starts coagulate.

To identify the antigens of a cancer in the blood and in exemplary embodiments, one can attach antibodies on the surface of the micro-channel. As the blood flows on top of the antibodies in the channel, the cancer antigens bind with pre-determined antibodies (e.g., which are related to cancer) on the surface of the channel.

The antibodies bonding with cancer antigens can determine the existence of cancer in a blood sample. The increased quantity of antigens that are involved in bonding can increase the accuracy in diagnosis of cancer in a given blood sample. Therefore, designing the micro-channel with feasibility for increased antigen-antibody bonding is important.

Other embodiments include not only to diagnose the cancer related antigens, but also to identify the percentage of existing cancer related antigens in blood. This can help the doctor to respond accordingly upon the seriousness of the patient condition.

It is noted that more than a half million deaths in the U.S. are because of cancer as per statistics. Out of which, many of the cancers are curable if identified in early stages. In general, for a person to get diagnosed with cancer is a very special scenario, which will not happen until the patient approaches the doctor with some health issue. But with a bio-chip based diagnostic assembly designed for cancer diagnosis, one can make this process a regular one (e.g., similar to a diabetes test).

An important impact of the bio-chip assembly designed for cancer diagnosis is that the diagnosis process can be simple and handy so that a person with substantially no medical knowledge can perform the cancer diagnosis. Additionally, the bio-chip based on the designed micro-channel can be manufactured at very low prices as there are not many expensive materials used in its manufacturing. Hence, the micro-channel based bio-chip can be a powerful tool to identify cancer at very early stages.

Currently, some researchers in the field are focused on the RBC flow characteristics at specially defined conditions. But defining the whole blood flow can represent the breakthrough that addresses many challenges currently existing in designing efficient and cost-effective cancer-diagnosing bio-chips as well as other bio-medical applications.

In certain embodiments and as discussed further below, the design and fabrication of an exemplary micro-channel of a bio-chip can be divided into the following steps: (i) manufacturing of a channel layer having a micro-channel (e.g., a PDMS channel layer having a hydrophilic micro-channel) and attaching cancer antibodies to the surfaces of the micro-channel, (ii) analysis of blood flow dynamics in the micro-channel, and (iii) sensing the cancer antigen qualitatively and quantitatively in the blood using a capacitance method with nano-electronics.

1. Manufacturing of a Channel Layer Having a Micro-Channel and Attaching Cancer Antibodies to the Surfaces of the Micro-Channel:

A micro-channel fabricated on a chip (e.g., PDMS chip) can be designed and fabricated with various surface treatments in order to have antibodies attached to the surface of the channel walls. A PDMS micro-channel can primarily be constructed using a soft lithography technique. As the PDMS is a hydrophobic material, it can be treated with an air plasma technique where a stable hydrophilic surface of $SiO_2$ is created at the walls of the micro-channel. An exemplary micro-channel fabricated for cancer diagnosis can be coated with antibodies on the walls of the channel to facilitate the antigen and antibody bonding. Since the antibodies that are attached are cancer specific, the antigens bonding to those antibodies will be cancer antigens in blood and thus can help one to identify the existence of cancer related antigens in a blood sample.

2. Analysis of Blood Flow Dynamics in the Micro-Channel:

In general and as shown in FIG. 1, blood is composed of plasma and RBCs (erythrocytes) for the majority of its volume. The percentage of plasma in blood is about 54% to about 55%. When plasma is considered individually, it behaves as a Newtonian fluid. Due to various molecular interactions between different components of plasma, the plasma has a higher viscosity. Plasma viscosity is about 1.10 to about 1.30 mPa s at about 37° C. which is close to 1.8 times of water. But due to the peculiar nature of the RBCs in the blood (constituting about 45%), the blood flow dynamics can change to be in a non-Newtonian form.

As RBCs are deformable in nature, the viscosity of blood varies with respect to the flow. The flow in the micro-channel is due to the capillary force and surface tension at the meniscus of the blood. So in order to define the blood flow in the micro-channel, the study of flow dynamics at the meniscus and at the vicinity of the erythrocytes is important. So in this step, the hemorheology is performed in the fabricated PDMS micro-channel.

Figure 2:
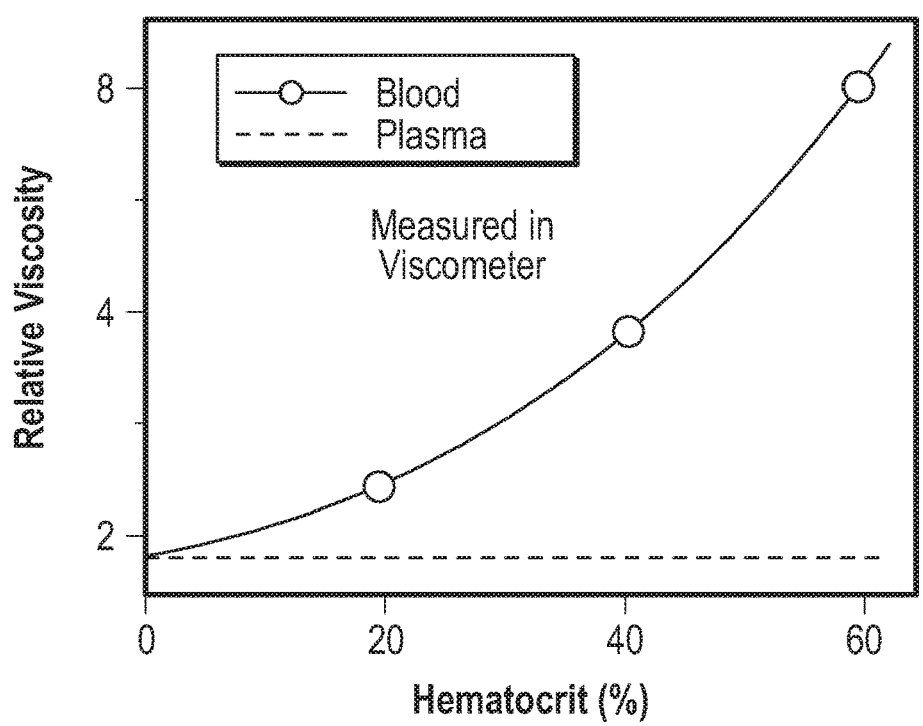
FIG. 2 shows a graph that explains the change on the viscosity phenomenon in blood with the percentage of erythrocytes in blood (Hematocrit)
Figure 3:
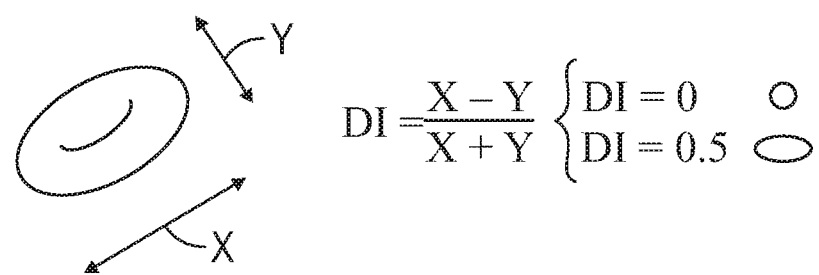
FIG. 3 shows a graph that explains the behavior of red blood cells ("RBCs") deformation index ("DI") increment with shear stress. The RBCs initial shape was assumed to be an ellipsoid and X & Y major (primary) and minor (secondary) axis lengths of the ellipse. The ambient fluid viscosity considered was 30 mPas and shear modulus as 20 N/m. It is observed from the graph that the deformations of RBCs are continuously increasing with increased shear stress.
Figure 3:
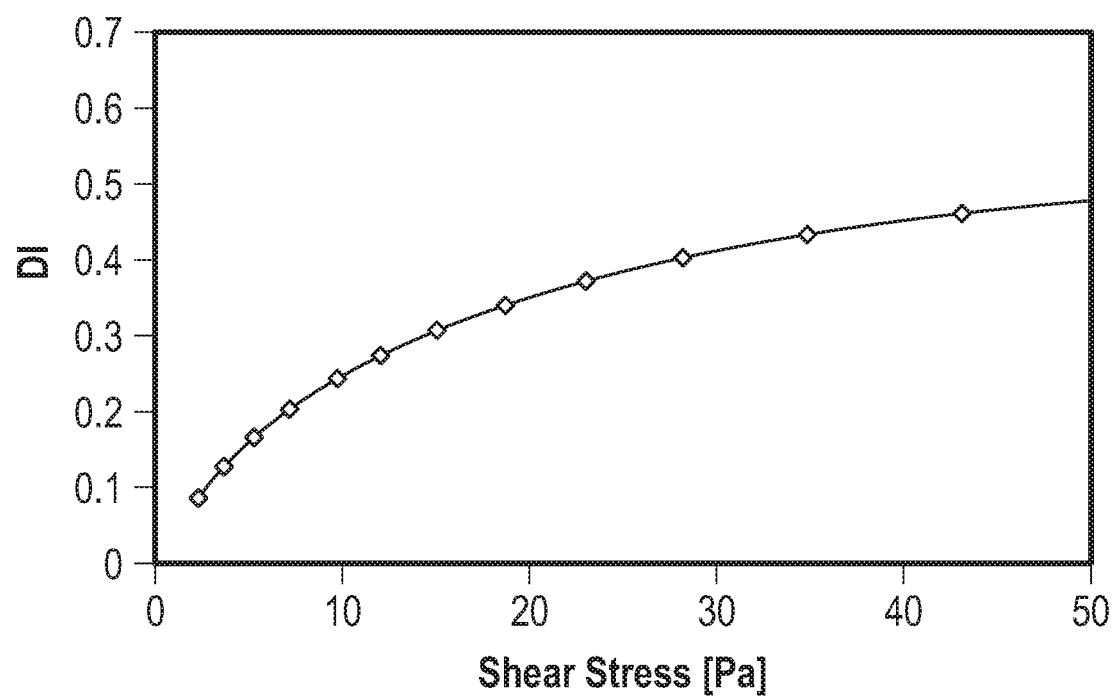

FIG. 2 shows a graph that explains the change on the viscosity phenomenon in blood with the percentage of erythrocytes in blood (Hematocrit). FIG. 3 shows a graph that explains the behavior of RBCs deformation index (DI) increment with shear stress. The RBCs initial shape was assumed to be an ellipsoid and X & Y major (primary) and minor (secondary) axis lengths of the ellipse. The ambient fluid viscosity considered was 30 mPas and shear modulus as 20 N/m. It is observed from FIG. 3 that the deformations of RBCs are continuously increasing with increased shear stress.

3. Sensing the Cancer Antigen Qualitatively and Quantitatively in the Blood Using a Capacitance Method with Nano-Electronics:

When the blood flows in the channel, the antigens in the blood will bond with the antibodies attached to the walls of the channel that are related to cancer. The antigens in a blood sample, which are bonded to antibodies attached to surfaces of the micro-channel, will show their existence. In exemplary embodiments, a capacitor can be fabricated with nano-scale electronics that can generate a digital signal when there is a bond formed between the antibody on the surface of a channel and to the antigen in the blood sample. Hence the identification of cancer related antigens in the blood can be made with a digital signal output. Thus, this exemplary nano-electronic sensor can be used to measure cancer antigens qualitatively and quantitatively in a blood sample.

Thus and in exemplary embodiments, micro-channel structures can be designed. Moreover, the micro-fabrication process for molds (e.g., PDMS molds) can be designed, and PDMS can be molded for making micro-channels.

Experiments and analysis with the optical-transparent micro-channels can be conducted to investigate the flow dynamics and behaviors in complex flows of base fluid (e.g., blood syrup), big deformable solid particles (e.g., mostly RBC, plates, white blood cells or WBC), and nanoparticles of bio-agents (e.g., antigens, antibodies). One can also determine the mechanism of the chemical reactions and sensing enhancement of the nanoparticle bio-agents on the microfluidic channel flow structures. Furthermore, one can implement an electrical sensing mechanism at the bottom of the micro-channels to get the signal of the chemical bio-agent reaction for disease diagnosis.

The fabrication related processes can include micro-chip (e.g., PDMS micro-chip) fabrication, and an electrical sensing implementation process using microfabrication facilities. Also a fine high resolution 3-D optical microscope system can be utilized.

In exemplary embodiments and as discussed further below, one can fabricate a micro-channel in PDMS material. Exemplary channel dimensions considered include a channel having about a 200 μm width and about a 60 μm depth, although the present disclosure is not limited thereto. Rather, it is noted that the channel can have other suitable widths/depths (e.g., 300 μm width and 100 μm depth; 200 μm width and 100 μm depth, etc.).

The micro-channel can be fabricated using a soft lithography technique, and can be treated with air plasma in order to convert the hydrophobic to hydrophilic surface at the walls of the channel. The cancer antibodies can be attached to the walls of the channel before the blood actually flows on/through it. As noted, the study of blood flow dynamics can be important for this research.

Step 1—Ascertaining the Dynamics at the Meniscus of Flow in the Channel:

The flow in the channel can be happening with no external force and the only driving force can be the capillary force and surface tension at the meniscus. Dynamics of the meniscus of the blood can be observed in order to regulate the flow. Since the surface tension at the meniscus of the blood is primary the driving force, the characteristics of the meniscus can be observed in detail.

Step 2—Identifying the Dynamics of the Blood Flow at Various Surface Roughnesses in the PDMS Micro Channel:

The blood flows through the PDMS micro-channel, and the micro-channel can be treated with various surface treatments. As such, the surface roughness on the channel can be influenced by the surface treatment made to the channel Since PDMS is generally a hydrophobic material, it can be treated with air plasma in order to convert it to a hydrophilic surface. The treatment of oxygen plasma on PDMS introduces polar functional groups, which is mainly the silanol group —Si(CH$_3$)2OH. This group can change the surface properties of PDMS from being hydrophobic to hydrophilic.

The channel can be chemically treated to convert the PDMS to hydrophilic and also to have the antibodies of cancer attached to the surfaces of the wall. So, studying the hemorheology in the micro-channel is another important step.

Step 3—Analysis of Erythrocytes (RBCs) Behavior in the PDMS Micro Channel:

Blood includes various biological elements like erythrocytes (RBCs), leukocytes (WBCs), thrombocytes (Platelets) and plasma. The plasma can have the majority of its composition as water and its flow behavior can be a Newtonian flow. RBCs are deformable bodies and flexible in their shapes and structures. An ideal blood sample can include 45% of RBCs, so the study of their behavior in the flow can be very decisive.

The viscosity of blood generally increases with increases in hematocrit. Even the plasma is considered as a Newtonian fluid, but the blood on the whole can be considered as non-Newtonian, just because of erythrocytes. The deformable structure of these RBCs creates varied viscosity in the flow. So identifying and analyzing the flow patterns in the vicinity of these RBCs can be important to define the flow of blood.

Step 4—Determining the Influence of Blood Coagulation on the Flow in the Micro-Channel:

In some embodiments, the antigen and antibody bonding in a micro-channel is not a time constraint mechanism. But blood due to its natural property of coagulation can influence the flow. Blood coagulation depends on various biological elements in blood. One can identify the influence of blood coagulation on blood flow in a micro-channel. The variation in viscosity of the blood over the flow period in the micro-channel is to be observed. By evaluating the viscosity variation over the flow period and flow length in the channel, the length of the micro-channel can be determined.

The evaluation of blood characteristics are useful for many reasons. Establishing the pivotal characteristics of blood flow in a micro-channel especially at the meniscus and erythrocytes and also determining the influence of a coagulation factor on flow can open doors for many advances (e.g., in the fields of bio-medical instrumentation, pharmacology, bio-mechanical, nano sciences etc.). Hemorheology is an important study for advancements in biomedical fluid devices. Exemplary studies can focus on the hemorheology and articulate research on blood flow in this field.

Step 5—Sensing the Antigens in the Blood Using Nano-Electronics:

In certain embodiments, a final step for the cancer diagnosis using an exemplary diagnostic chip (e.g., PDMS chip) is to sense the cancer antigens in the micro blood sample quantitatively and qualitatively. In order to sense these antigens which are bonded to antibodies attached to a micro-channel, a capacitor method can be used to provide a digital signal output. These capacitors can be fabricated using nano-electronics. Once these antigens are identified, the quantitative analysis can be implemented to identify the seriousness of the cancer in the blood specimen.

As noted, the present disclosure provides for the fabrication of exemplary micro-channels, and provides for the evaluation of the blood flow phenomenon at various surface roughnesses. The PDMS micro-channel can be designed in order to facilitate the blood to flow continuously and uninterruptedly. Once the channel is fabricated as designed, it can be surface treated to convert it to hydrophilic. Thus, after the micro-channel is fabricated with the specified features and dimensions, the blood flow phenomenon can be examined at specific locations (e.g., meniscus, vicinity of erythrocytes, etc.).

In exemplary embodiments, the present disclosure provides for the fabrication of micro-channels of dimensions in micro-scale. A Karl Suss MA6 Mask Aligner is a top and bottom side contact printer used for fine lithography down to 1 micron or better. In certain embodiments, micro-channels can be fabricated on PDMS material using the Karl Suss MA6 Mask Aligner with a lithography technique. As the specifications can be reached to 1 micron using this equipment, it can be very helpful to design the micro channels with fine specifications in the internal edges and surfaces of the channels. The channels can be provided with fine notches on the surface of the walls to prevent the back flow which can be achieved with instruments like the Karl Suss MA6 Mask Aligner.

Another focus of the present disclosure is to analyze the blood flow characteristics in a micro-channel in order to define and regulate the blood flow on the cancer antibodies at the surface of the channel. To study the flow dynamics of blood at the micro level and to observe the RBCs (e.g., erythrocytes—sizing at 6-8 micro-meters) behavior in the flow, it can be helpful to work with Scanning Electron Microscopes (e.g., Hitachi S-4800 SEM). As the Hitachi S-4800 field emission scanning electron microscope features a maximum resolution of about 1.0 nm and a variable acceleration voltage of 0.5 to 30 kV and also having both secondary electron and backscattering electron detectors availability for imaging, it can be helpful to examine the blood flow phenomenon on a SEM. As a SEM provides Scanning Transmission Electron Microscopy ("STEM") imaging capability at 30 kV, it can be useful for STEM imaging of the biological samples. As such, since some exemplary observations and analysis are based on micro blood samples, working on a SEM can be useful.

Figure 4:
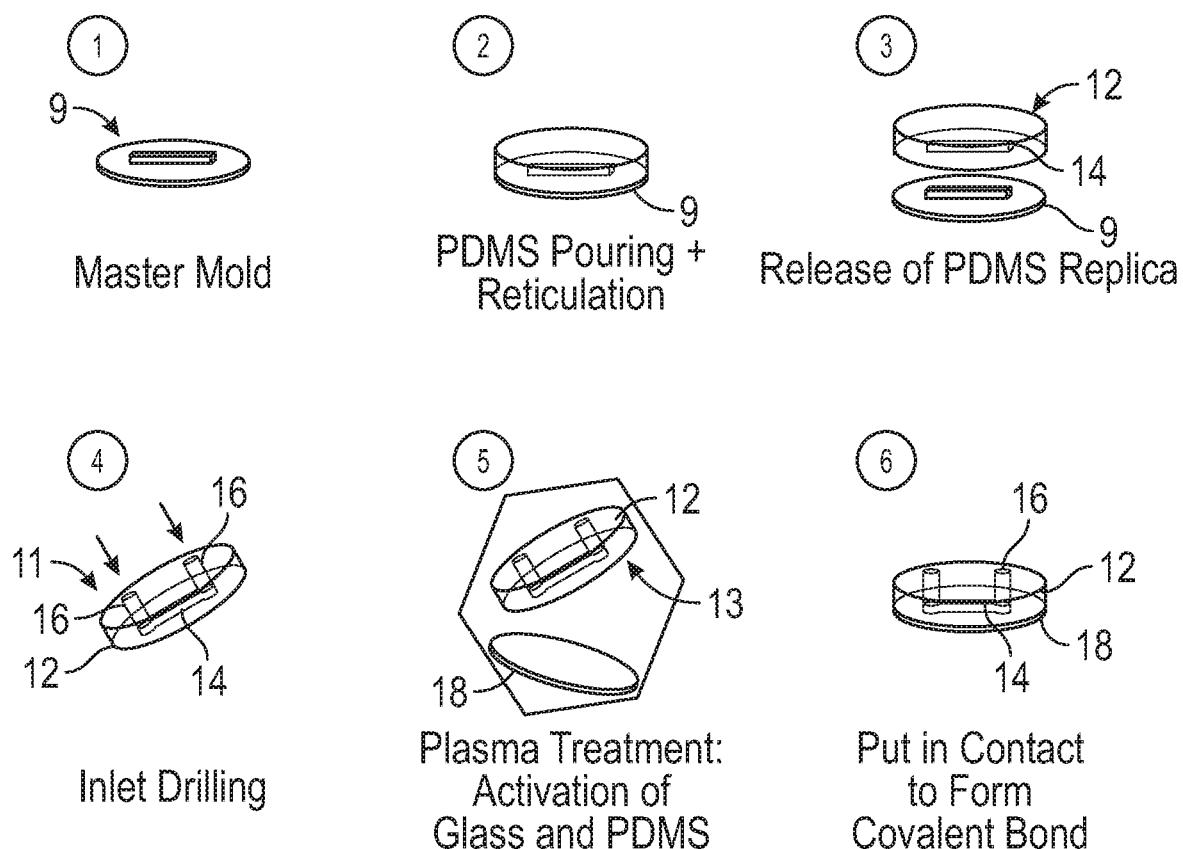
FIG. 4 depicts some exemplary processing steps for fabricating a micro-channel layer and converting the micro-channel of the micro-channel layer from hydrophobic to hydrophilic.

FIG. 4 depicts some exemplary processing steps for fabricating a micro-channel layer 12 and converting the micro-channel 14 of the micro-channel layer 12 from hydrophobic to hydrophilic.

In exemplary embodiments, disease diagnosis (e.g., cancer diagnosis) is performed via a channel layer 12 of a micro-fluidic chip assembly using a micro-blood sample. The micro-fluidic chip assembly includes a channel layer 12 (e.g., a polydimethylsiloxane or PDMS micro-channel layer 12) through which the cancer affected patient's blood is flowed through. The micro-channel 14 of the channel layer 12 can be designed in such a way that the blood is flowed by its natural capillary force without any external force. Techniques like electro-wetting and plasma oxidation can be applied on the channel 14 of the channel layer 12 to convert it from hydrophobic to hydrophilic. Some inlet or well structures 16 can be introduced at the surfaces of the channel layer 12 in order to facilitate blood for mixing and particle (e.g., Erythrocytes—RBC) transportation.

The surfaces of the walls of the channel 14 can be treated with antibodies at specified lengths of the channel 14. As the antibodies which are coated to the surface of the channel 14 are predetermined, the antigens that are bonded to these antibodies are evident. The existence of cancer antigens in the blood sample that is flowed through the micro-channel 14 provides the evidence of cancer. This qualitative approach is helpful to examine the existence of cancer in patient blood.

The computation of bonding formed between antigen and antibody in the specified length of the channel 14 for a known volume of blood sample gives the quantitative results of the cancer diagnosis. As discussed further below, the antigen and antibody bonding is captured by applying the principle of a capacitor whose output can be a digital signal. These digital signals can be displayed on a screen for better visualization of the results.

As shown in FIG. 4, in step 1 a master mold 9 is provided. The master mold 9 can be fabricated from a variety of materials (e.g., polymers, plastic, glass, etc.).

In step 2, a channel layer material 12 (e.g., PDMS) is poured on the master mold 9, and in step 3 the channel layer material 12 is released from the master mold 9 to form the channel layer 12 having the micro-channel 14.

In step 4 of FIG. 4, inlet/outlet or well structures 16 can be fabricated or drilled at a top surface 11 of the channel layer 12 until they connect with the channel 14. Thus, the inlet and outlets wells 16 for the flow in the channel 14 can be fabricated as part of the channel layer 12.

Step 5 shows that techniques like electro-wetting or plasma oxidation can be applied on the channel 14 of the channel layer 12 to convert it from hydrophobic to hydrophilic. The channel layer 12 can then be mounted to a substrate 18 in step 6 to seal the bottom surface 13 of the channel layer 12.

As noted, exemplary channel 14 dimensions of channel layer 12 include a channel 14 having a 200 μm width and a 60 μm depth, although the present disclosure is not limited thereto. Rather, it is again noted that the channel 14 can have other suitable widths/depths (e.g., 300 μm width and 100 μm depth; 200 μm width and 100 μm depth, etc.).

The micro-channel 14 can be fabricated using a soft lithography technique and treated with air plasma in order to convert the hydrophobic surface to a hydrophilic surface at the walls of the channel 14. The cancer antibodies can be attached to the walls of the channel 14 before the blood flows on/through channel 14.

Figure 5:
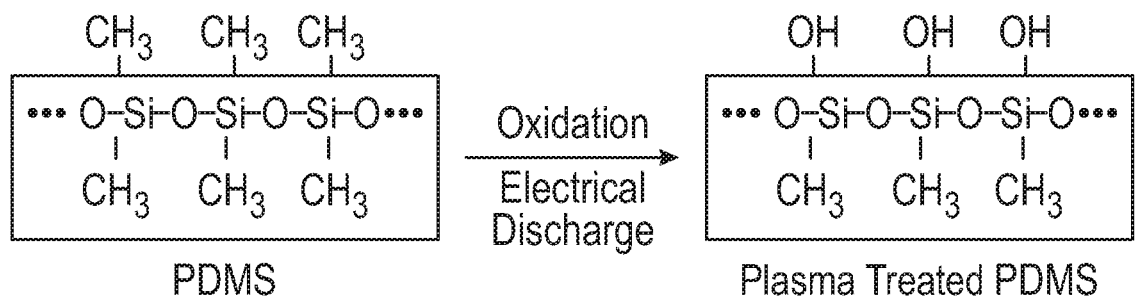
FIG. 5 shows an exemplary schematic of the oxygen plasma treatment of a polydimethylsiloxane or PDMS channel.

FIG. 5 shows an exemplary schematic of the oxygen plasma treatment of a PDMS channel 14 (e.g., during step 5 of FIG. 4).

Figure 6:
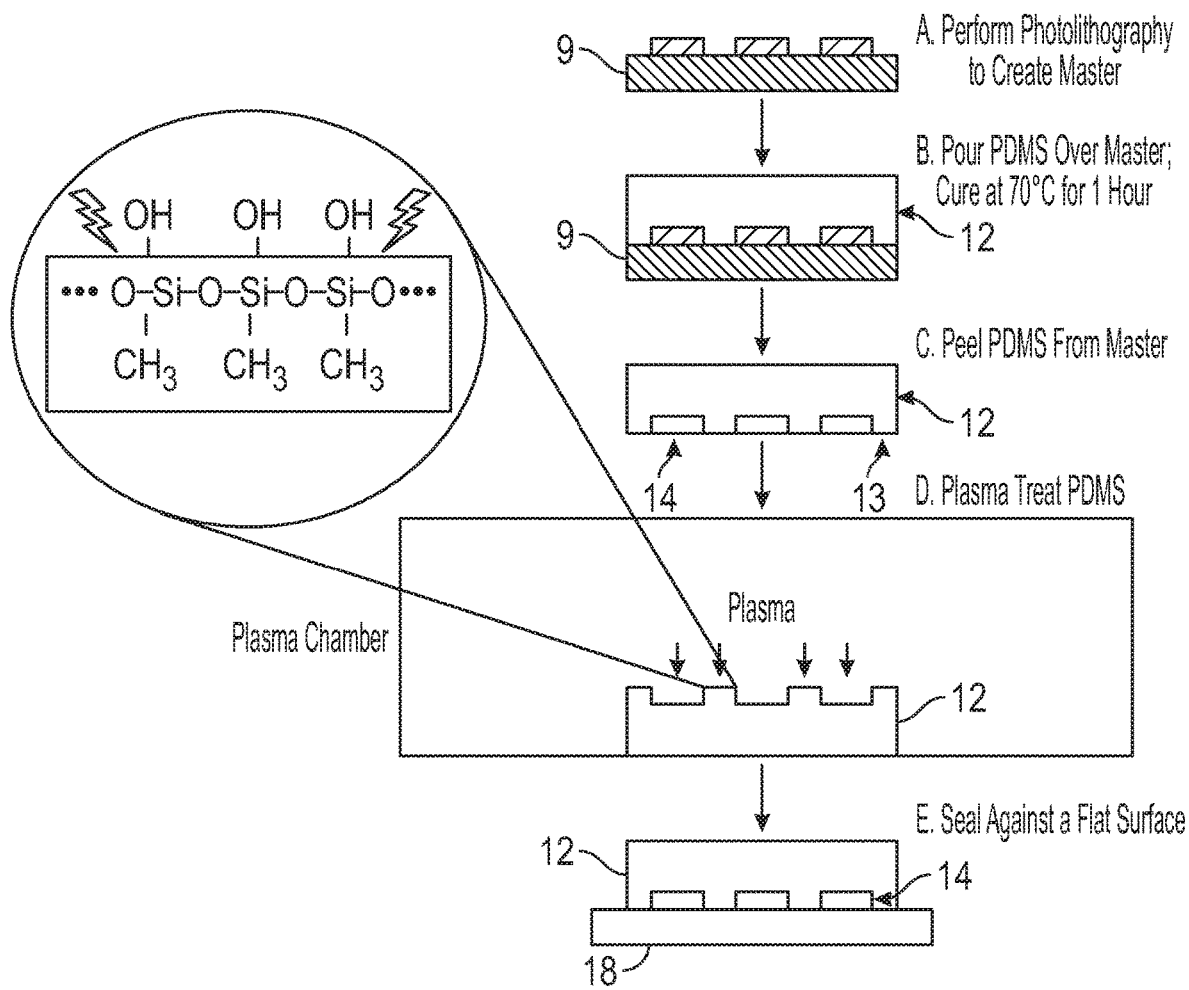
FIG. 6 shows other exemplary processing steps for fabricating a micro-channel layer having a PDMS micro-channel that has undergone plasma treatment.

FIG. 6 shows other exemplary processing steps for fabricating a micro-channel layer 12 having a PDMS micro-channel 14 that has undergone plasma treatment. As shown in Step A of FIG. 6, a master mold 9 is provided by performing photolithography to create the master mold 9. In step B, a channel layer material 12 (e.g., PDMS) is poured on the master mold 9, and then is thereafter cured (e.g., 70° C. for 1 hour). In Step C, the channel layer material 12 (e.g., PDMS) is released/peeled from the master mold 9 to form the channel layer 12 having the micro-channel 14. As shown in Step D, the channel layer 12 is then plasma treated in a plasma chamber. In Step E, the channel layer 12 is sealed against a substrate 18 (e.g., substrate 18 having a flat surface) to seal the bottom surface 13 of the channel layer 12.

Figure 7:
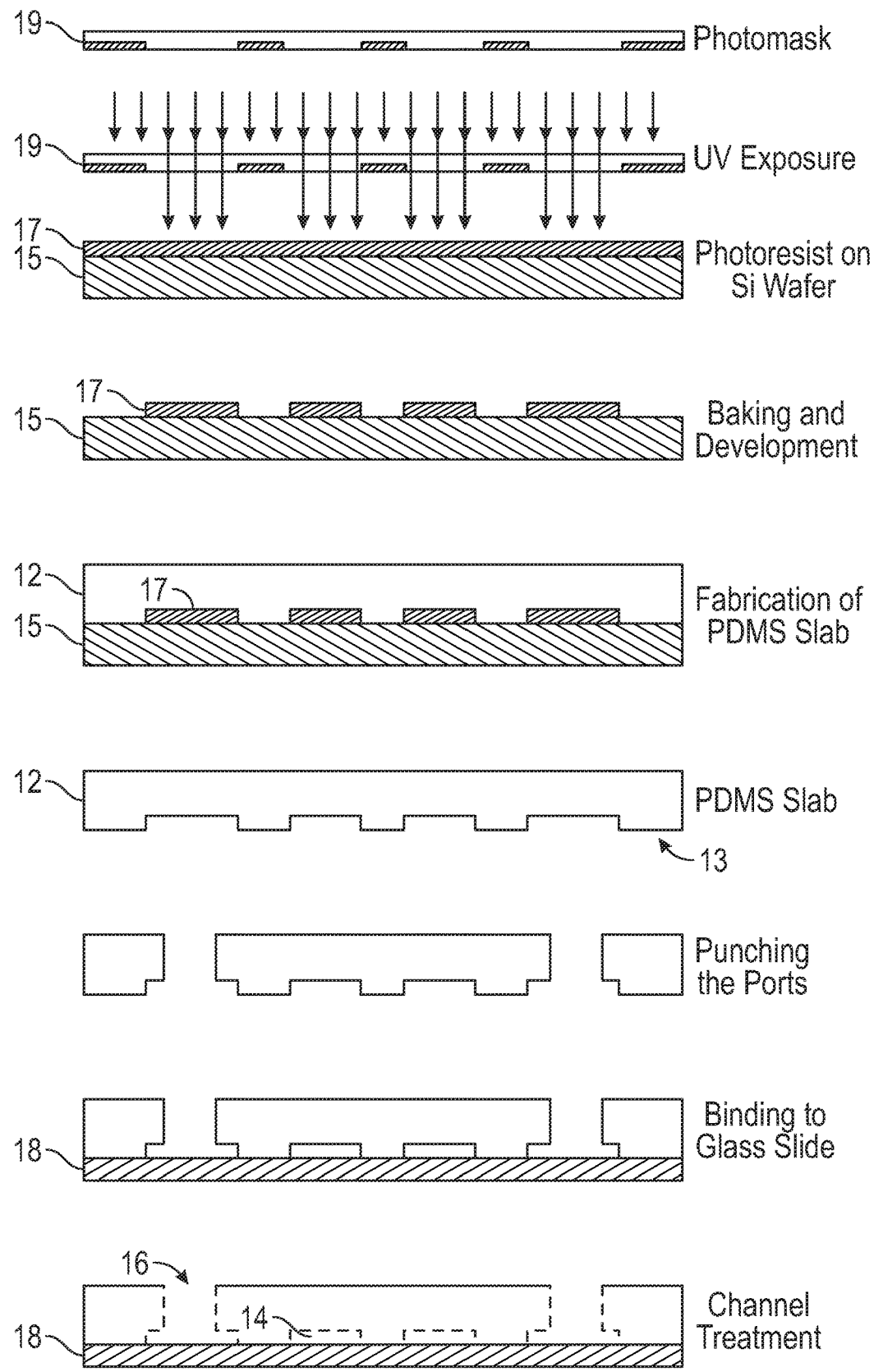
FIG. 7 shows exemplary processing steps for fabricating a micro-channel layer having a PDMS micro-channel utilizing lithography and air plasma techniques.

FIG. 7 shows exemplary processing steps for fabricating a micro-channel layer 12 having a PDMS micro-channel 14 utilizing lithography and air plasma techniques.

As shown in FIG. 7, a silicon wafer 15 can be provided. The silicon wafer 15 can be cleaned with acetone, isopropanol alcohol and de-ionized ("DI") water. The silicon wafer 15 can be dehydrated at 115° C. for about one minute and then kept on a cold plate to attain a normalized temperature.

Next, a photoresist layer 17 can be deposited on top of the silicon wafer 15. The silicon wafer 15 can then be positioned on a spinner at 1200 to 2000 rpm for about a minute to remove excess material from the deposited photoresist layer 17, thereby providing a thin layer (e.g., micro-meters) of deposited photoresist layer 17 and silicon wafer 15. The wafer 15 with deposited photoresist 17 can then be soft baked at about 115° C. for about a minute to dry the photoresist layer 17 (FIG. 7—Photoresist on Si wafer).

The wafer 15 with deposited photoresist 17 can then be placed on a UV light exposure tool of a layering machine with an exposure time of 12 seconds. The wafer 15 with deposited photoresist 17 can then be covered by photomask 19. It is noted that the photomask 19 can be fabricated per the design pattern of the desired shape of the micro-channel 14. Due to the UV rays exposure, the area which is not covered by the photomask 19 will become soft.

The photomask 19 can then be removed carefully from the wafer 15. The wafer 15 can then be chemically treated (e.g., with MF-319) and then spun. After, the wafer 15 with remaining photoresist 17 can be treated with DI water and then dried with a nitrogen gun to remove water.

As shown in FIG. 7, a channel layer material 12 (e.g., PDMS) can then poured on the wafer 15 with remaining photoresist 17.

Prior to pouring, the channel layer material 12 (e.g., PDMS) can be blended with a curing agent. The channel layer material 12 (PDMS base) can be blended with a curing agent in proper proportion (e.g., 1:10). For example, the channel layer material 12 (PDMS base) can be 10 times that of the curing agent (PDMS curing agent). The channel layer material 12 and curing agent can be whicked vigorously with a spatula. Thorough mixing (about 10 minutes) can be provided to ensure that the curing agent is uniformly distributed. This can ensure that the final channel layer material 12 mold is uniformly cross-linked. The mixture can then be kept in a desicator to make the trapped air bubbles escape. For example, the mixture can be kept in a bell-jar desicator connected to a vacuum pump for about one hour.

The highly viscous channel layer material 12 (e.g., PDMS) can be allowed to flow on the wafer 15 with remaining photoresist 17 to form a blob atop the mold of wafer 15 with remaining photoresist 17. Spinning will even the blob out, with moderate edge bead effects. The channel layer material 12 (PDMS) can then be cured. Curing can be done by placing the channel layer material 12 (PDMS) on the wafer 15 with remaining photoresist 17 on a hot plate at 150° C. for about 6 to 8 minutes.

After the channel layer material 12 (PDMS) is suitably cured, the application of steady pressure should allow the channel layer material 12 to peel away from the mold (wafer 15 with remaining photoresist 17) with ease. It is noted that the channel layer material 12 surface can be highly inert. To make it more adhesive, to bond it to glass/substrate 18 or help coat metals on it, a freshly prepared channel layer material 12 substrate (e.g., PDMS substrate) can be exposed to 200 W RF plasma for about 20 seconds. This will break some crosslinks at the surface and make it more reactive.

One can convert the PDMS mold or channel layer 12 to hydrophilic from hydrophobic utilizing an oxygen plasma treatment. The treatment of oxygen plasma on channel layer material 12 (e.g., PDMS) introduces polar functional groups which is mainly the silanol group (SiOH). This group changes the surface properties of channel layer material 12 (PDMS) from being hydrophobic to hydrophilic. After the plasma treatment, the channel layer material 12 can be immersed in a container filled with de-ionized (DI) water. Air bubbles can be removed by injecting DI water through the access holes or wells 16 and storing the channel layer 12 in a vacuum chamber for some time (e.g., seven days).

As shown in FIG. 7, the channel layer 12 can then be sealed against a substrate 18 (e.g., substrate 18 having a flat surface) to seal the bottom surface 13 of the channel layer 12.

Figure 8:
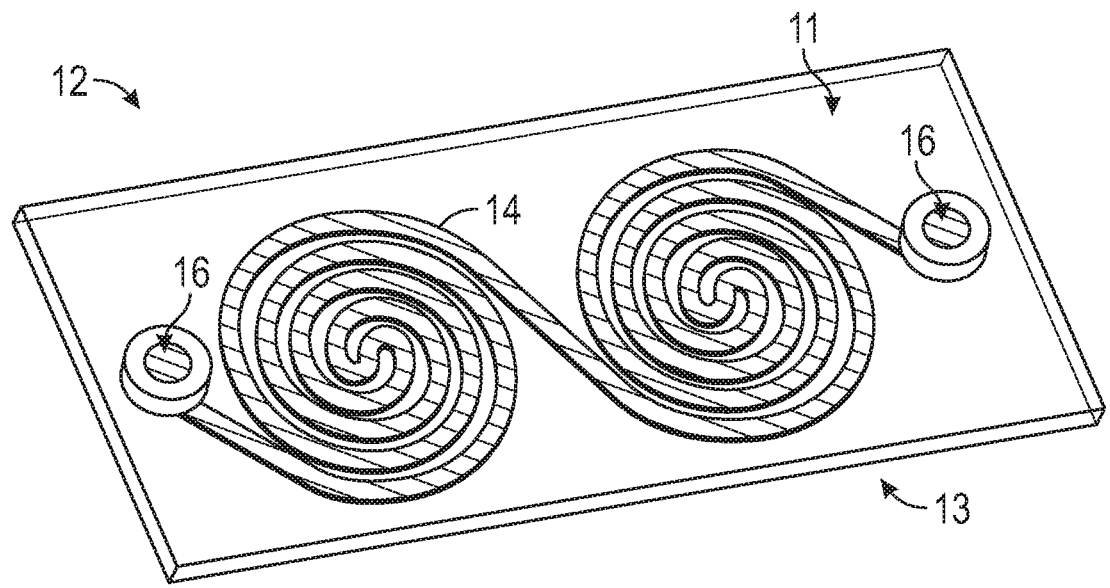
FIG. 8 is a top side perspective view of an exemplary channel layer.
Figure 9:
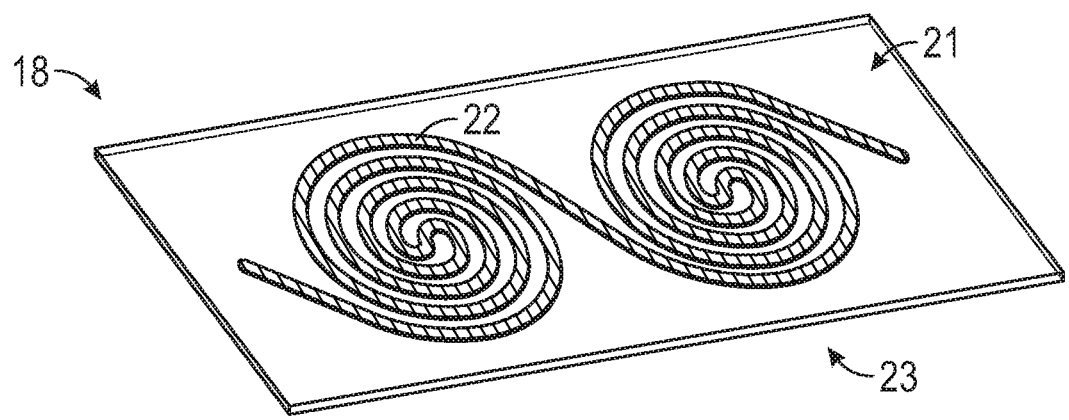
FIG. 9 is a top side perspective view of an exemplary insulation layer.

FIG. 8 shows a top side perspective view of an exemplary channel layer 12 fabricated according to embodiments of the present disclosure. FIG. 9 is a top side perspective view of an exemplary substrate or insulation layer 18.

As shown in FIG. 8, the micro-channel 14 takes the form of a substantially spiral-shaped channel 14 (e.g., a spiral micro-channel 14 connected in series in channel layer 12). Exemplary channel 14 extends from the bottom surface 13 toward the top surface 11 a distance of about 60 μm, with the channel 14 ending at a point between the top and bottom surfaces 11, 13 (e.g., channel 14 does not extend from surface 13 to surface 11). The width of exemplary channel is about 200 μm across, although the present disclosure is not limited thereto. Wells 16 can be drilled through top surface 11 of the channel layer 12 until they connect with the channel 14 at each end of channel 14.

As noted, FIG. 9 is a top side perspective view of an exemplary substrate or insulation layer 18, with the insulation layer 18 including a top surface 21 and a bottom surface 23. Exemplary insulation layer 18 takes the form of a silicon oxide wafer layer 18, although the present disclosure is not limited thereto. The top surface 21 of insulation layer includes a coating 22 of antibodies (e.g., cancer antibodies). Exemplary coating 22 takes the form a substantially spiral-shaped coating 22 that substantially matches the spiral shape of channel 14.

During fabrication of diagnostic assembly 10 (FIG. 11), the bottom surface 13 of channel layer 12 is mounted to the top surface 21 of substrate/insulation layer 18 to seal the bottom surface 13 of the channel layer 12, with the coating 22 being positioned under the channel 14.

Stated another way, the substrate/insulation layer 18 (e.g., silicon oxide wafer layer 18) covers the bottom surface 13 of the channel layer 12 (e.g., PDMS layer 12), thereby closing and sealing the open channel 14 on the bottom surface 13, which converts the open channel/cavity 14 to a closed channel 14 at surface 13. See also FIG. 7.

The cancer antibodies of coating 22 are attached to the insulation layer 18 in order to facilitate the antigen and antibody bonding during operation of assembly 10. In exemplary embodiments, the antibody coating 22 is placed at the locations where the micro-channel 14 interacts with the insulation layer 18 (e.g., coating 22 takes a shape/form that substantially matches the shape/form of channel 14, with the coating 22 positioned underneath channel 14). As the mounted insulation layer 18 is the bottom surface of channel 14, when blood flows in and through channel 14, the antigens of cancer in the blood will react with antibodies of coating 22 (which is coated on the surface of layer 18). In other embodiments, coating 22 can include antigens, and be configured and adapted to detect antibodies in the sample (e.g., blood).

Figure 10:
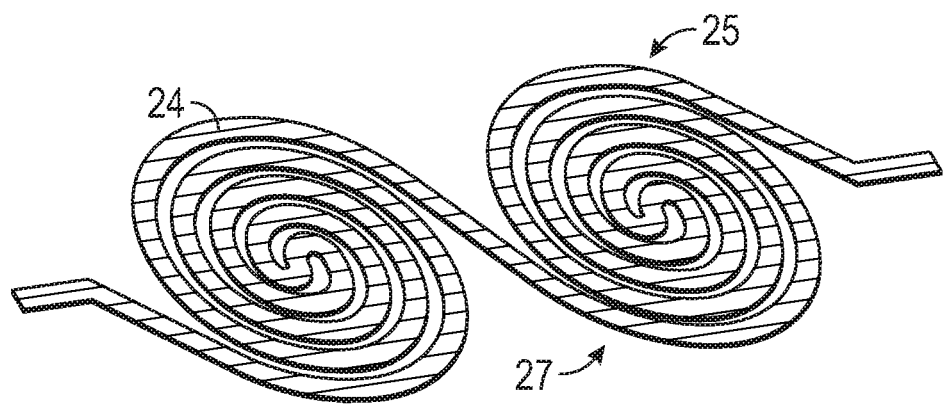
FIG. 10 is a top side perspective view of an exemplary circuit layer.

FIG. 10 is a top side perspective view of an exemplary circuit layer 24, with the circuit layer 24 including a top surface 25 and a bottom surface 27, and with the circuit layer 24 to function as a capacitor. For example, exemplary circuit layer 24 takes the form of a substantially spiral-shaped layer 24 that substantially matches the spiral shape of channel 14 and/or coating 22.

During fabrication of diagnostic assembly 10 (FIG. 11), the bottom surface 23 of insulation layer 18 is mounted to the top surface 25 of circuit layer 24, with the circuit layer 24 (e.g., spiral-shaped circuit layer 24) being positioned under the coating 22 (e.g., spiral coating 22). In general, circuit layer 24 can take a shape/form that substantially matches the shape/form of coating 22 and/or channel 14, with the circuit layer 24 positioned underneath bottom surface 23 of layer 18.

As such, there is a circuit layer 24 arranged below the insulation layer 18 similar to the shape of the channel 14 to create a capacitor effect and generate electric pulses based on the bonding of antigens and antibodies in the channel 14 (e.g., based on interactions of the fluid flow in the channel 14 with the coated area 22). Therefore and by utilizing this capacitor method of assembly 10, one can diagnose the bonding of antigen and antibody electronically.

Figure 11:
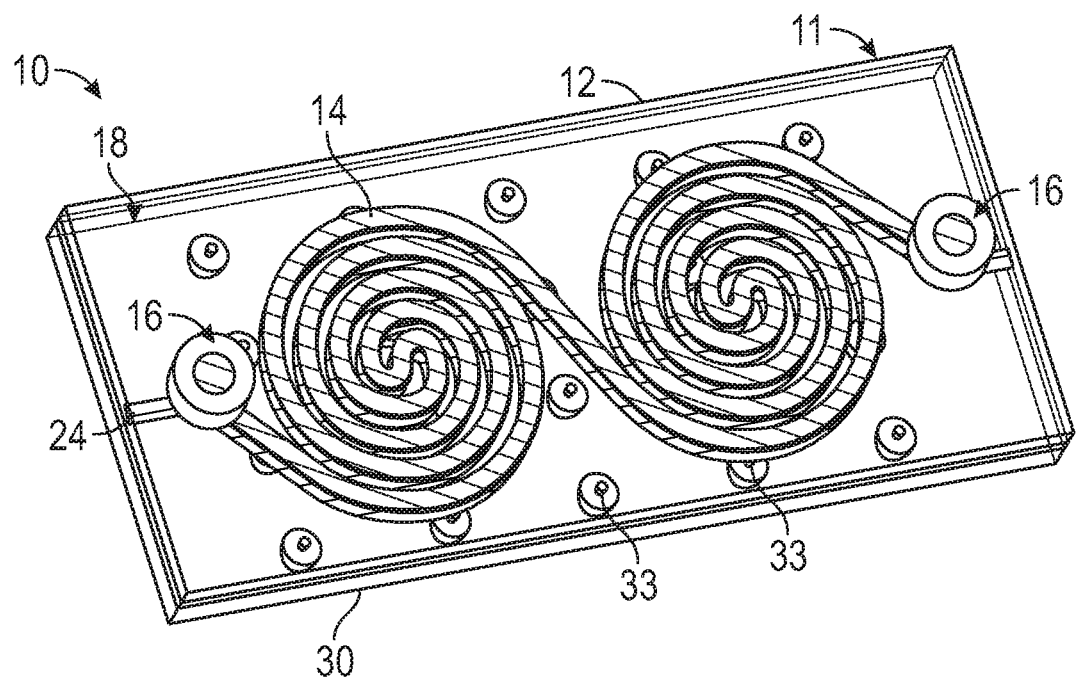
FIG. 11 is a top side perspective view of an exemplary diagnostic assembly.
Figure 12:
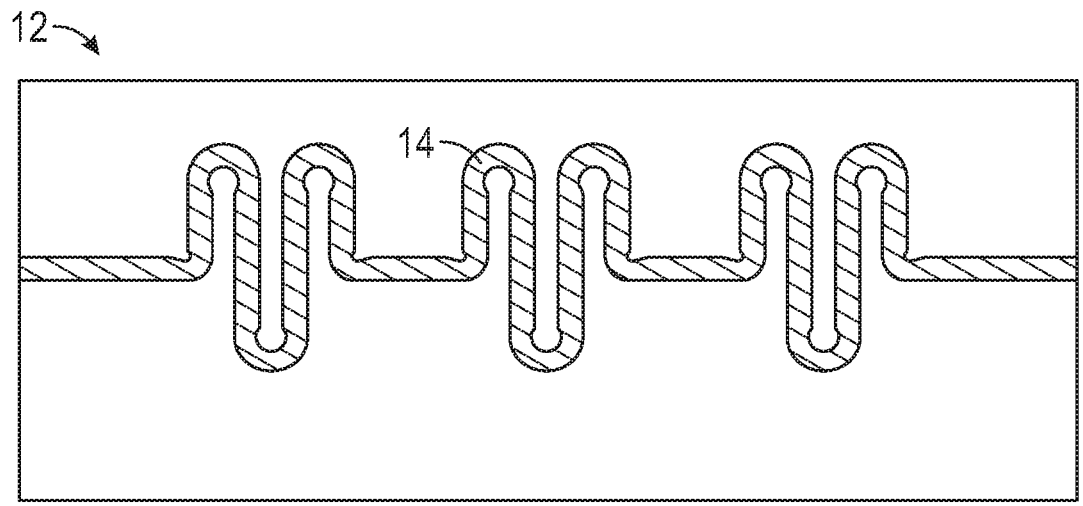
FIGS. 12-25 depict alternative shapes and designs of a channel of a channel layer.
Figure 13:
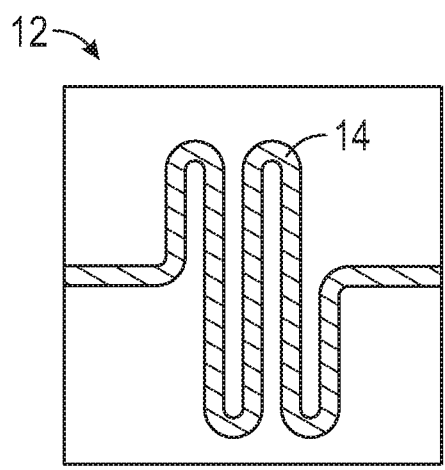
Figure 14:
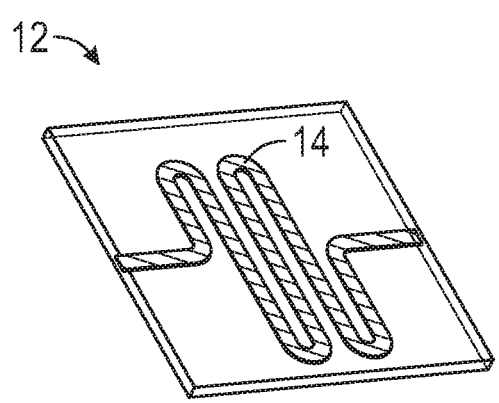
Figure 15:
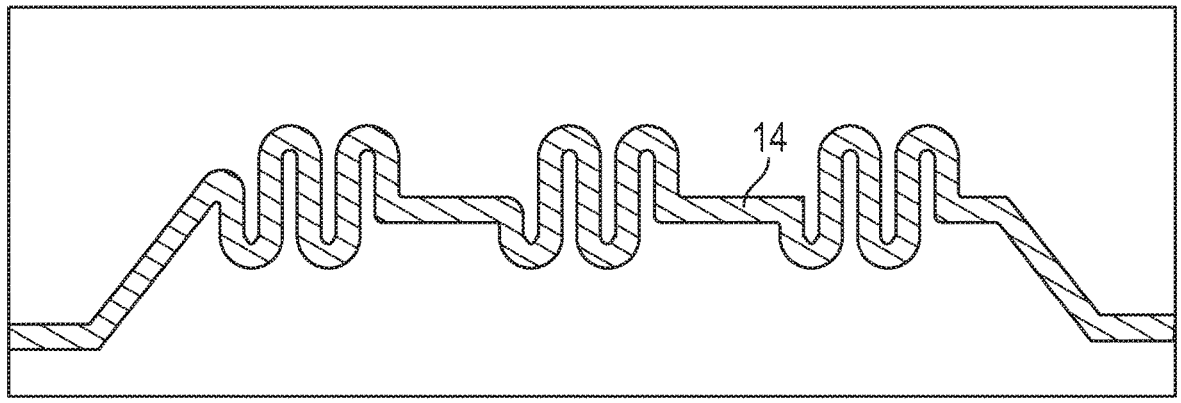

As shown in FIG. 11, diagnostic assembly 10 can also include a base member 30 mounted beneath the bottom surface 27 of the circuit layer 24 and/or beneath bottom surface 23 of insulation layer 18. Exemplary base member 30 includes a plurality of lights 33 (e.g., LED lights 33). As such, the lights 33 arranged beneath the circuit layer 24 can help in acquiring the signal from the circuit layer 24 and display the electrical signals in the form of lights 33 (e.g., LED lighting). As such, one can acquire the results much clearer using the LED lights 33.

Figure 16:
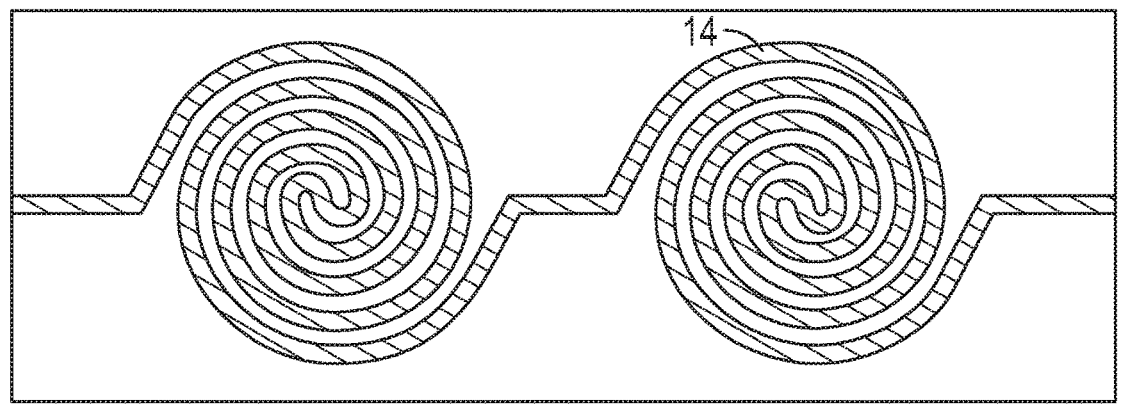
Figure 17:
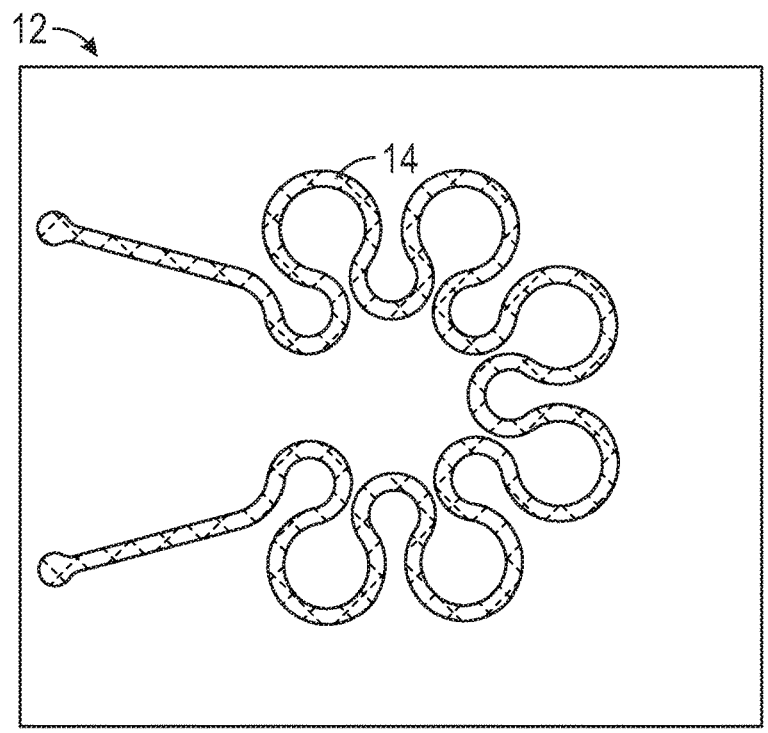
Figure 18:
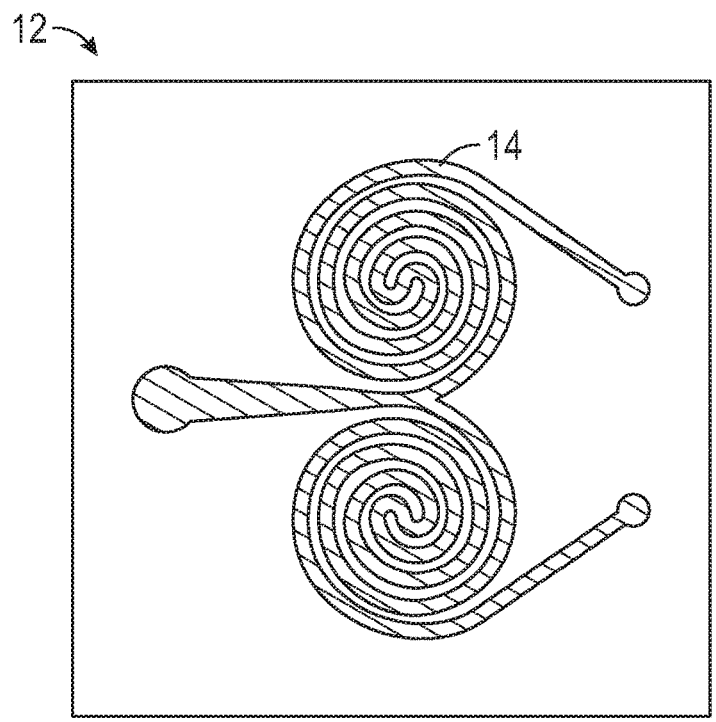
Figure 19:
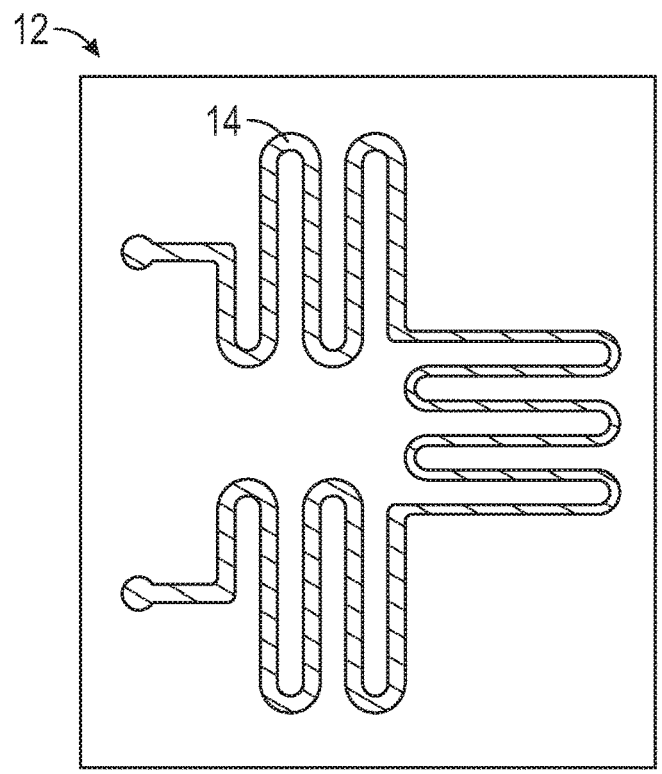
Figure 20:
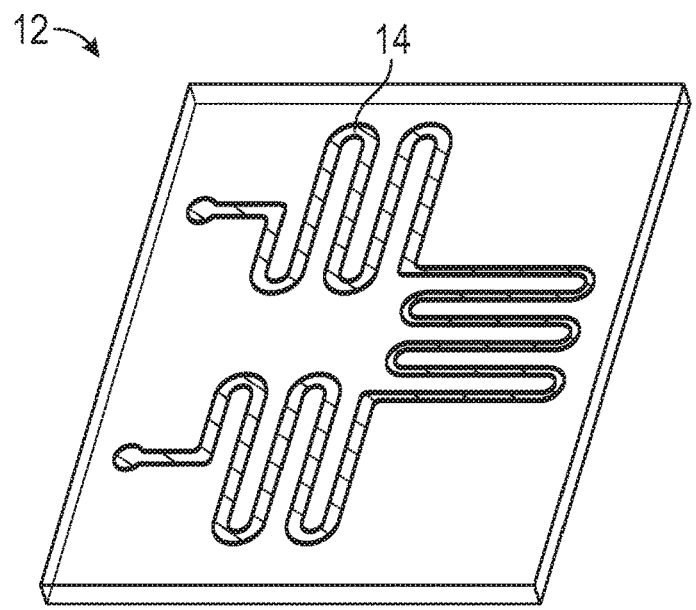
Figure 21:
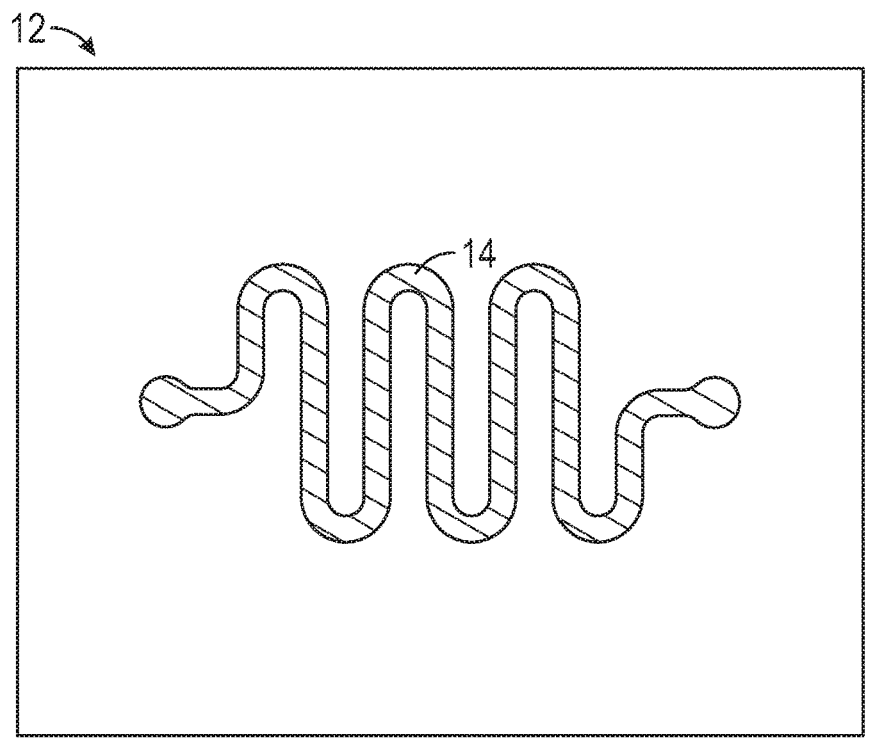
Figure 22:
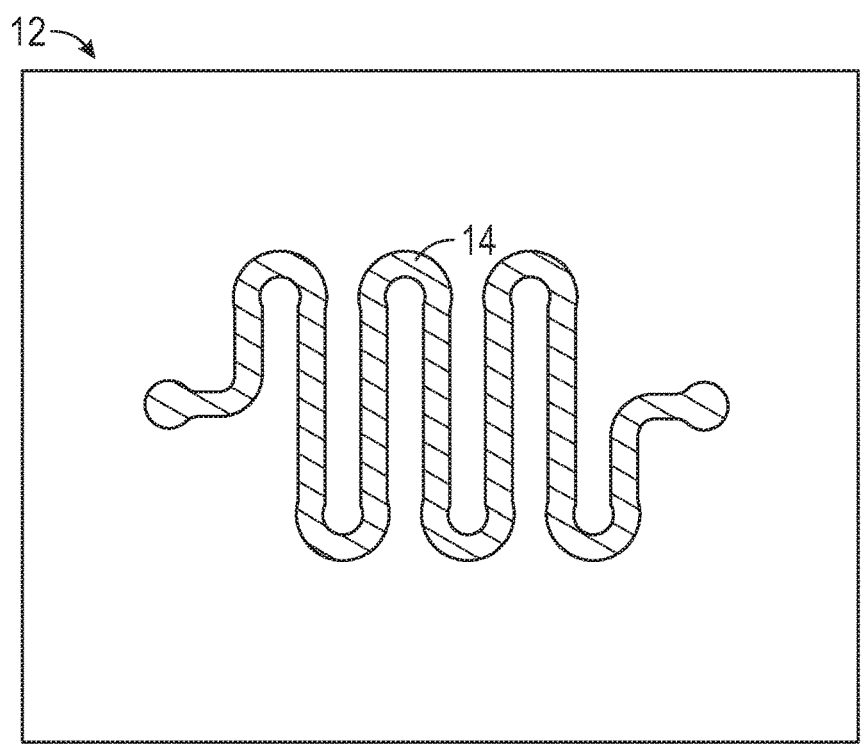
Figure 23:
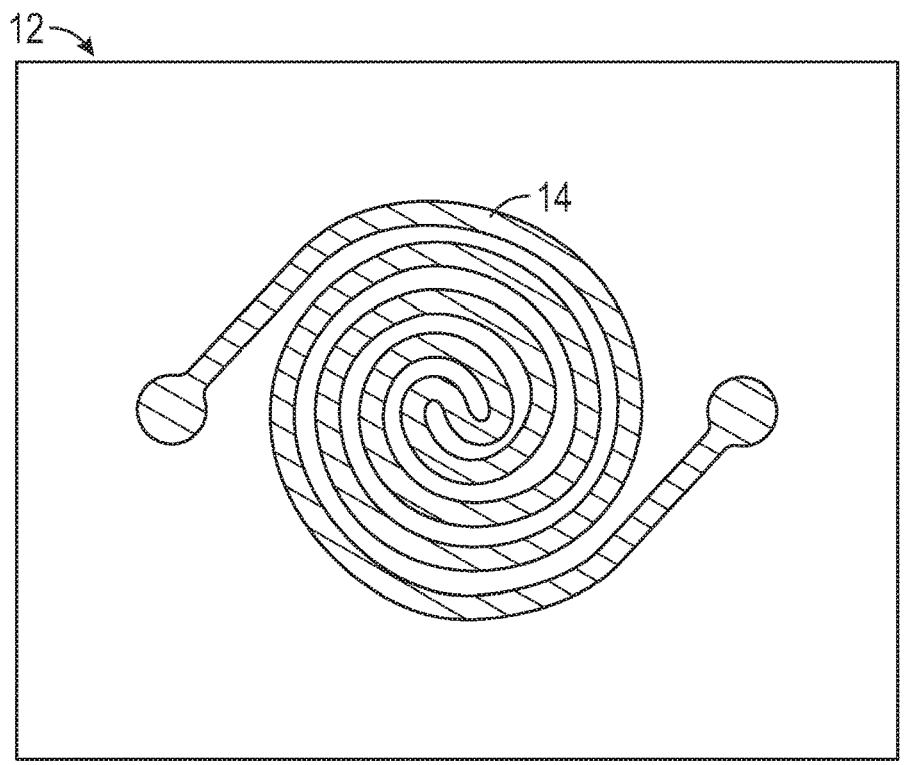
Figure 24:
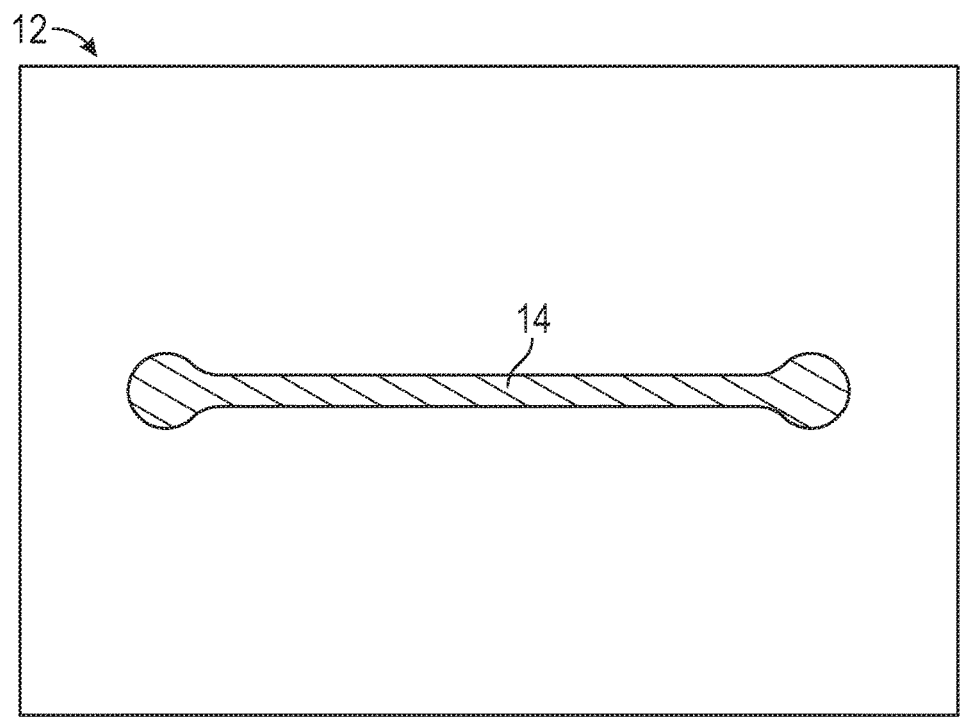

FIGS. 12-25 depict alternative shapes and designs of channel 14 of channel layer 12 (e.g., serpentine, spiral, straight channels 14, etc.). For example and as shown in FIG. 16, channel 14 can include spacing between the antigen and antibody sensing areas. FIG. 17 depicts a serpentine micro channel 14 design in a circular pattern with 200 μm width and 60 μm depth. FIG. 18 depicts a spiral microchannel 14 design connected in parallel to sense different cancer antigens. FIGS. 19-20 depict a serpentine microchannel 14 design with variable channel 14 widths to control the flow rate in the channel 14. As shown in FIGS. 12-25, channels 14 can be interconnected in multiples and in various patterns (e.g., series, parallel, circular, zig-zag, etc.). As shown in FIG. 22, the channel 14 can include circular edges throughout its length.

Figure 25:
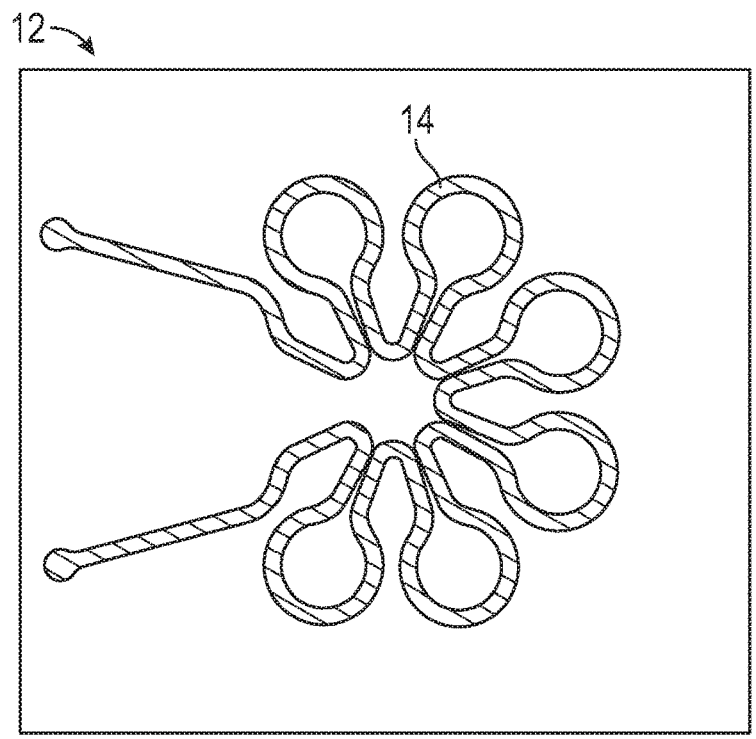
Figure 26:
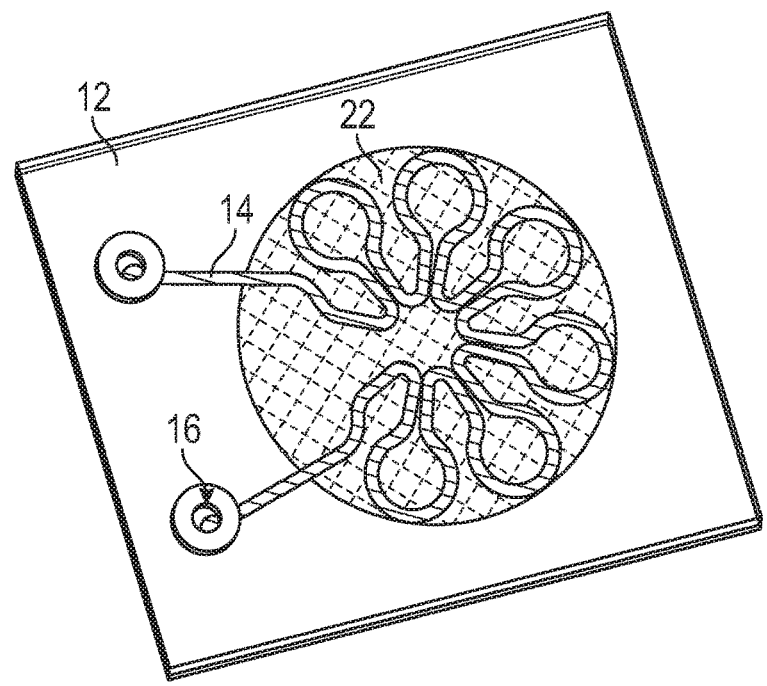
FIG. 26 shows an alternative diagnostic assembly having an alternative insulation layer.

As shown in FIG. 25, channel 14 can be in the form of bulb-shaped micro-channel 14 design in a circular pattern (e.g., with 200 μm width and 60 μm depth). As such and in some embodiments as shown in FIG. 26, the insulation layer 18 can include a coating 22 that is substantially circular in shape, with the diameter of the sensing/coating area 22 covering a circular area that substantially encompasses the areas of travel of channel 14 instead of substantially conforming to just the shape of the channel 14 itself.

Figure 27:
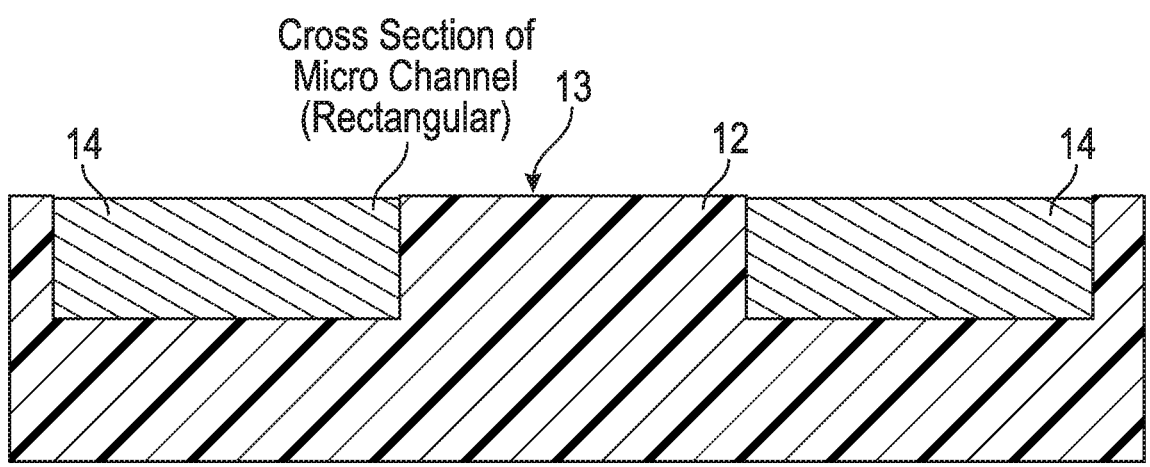
FIG. 27 is a side view of an exemplary channel layer.

FIG. 27 depicts a side view of an exemplary channel layer 12 with a channel 14 having a cross-sectional shape that is substantially rectangular. However, it is noted that the cross-sectional shape of channel 14 can take a variety of shapes/forms (e.g., square, eclipse-shaped, circular, rhombus, trapezoid, polygonal, etc.).

Figure 28:
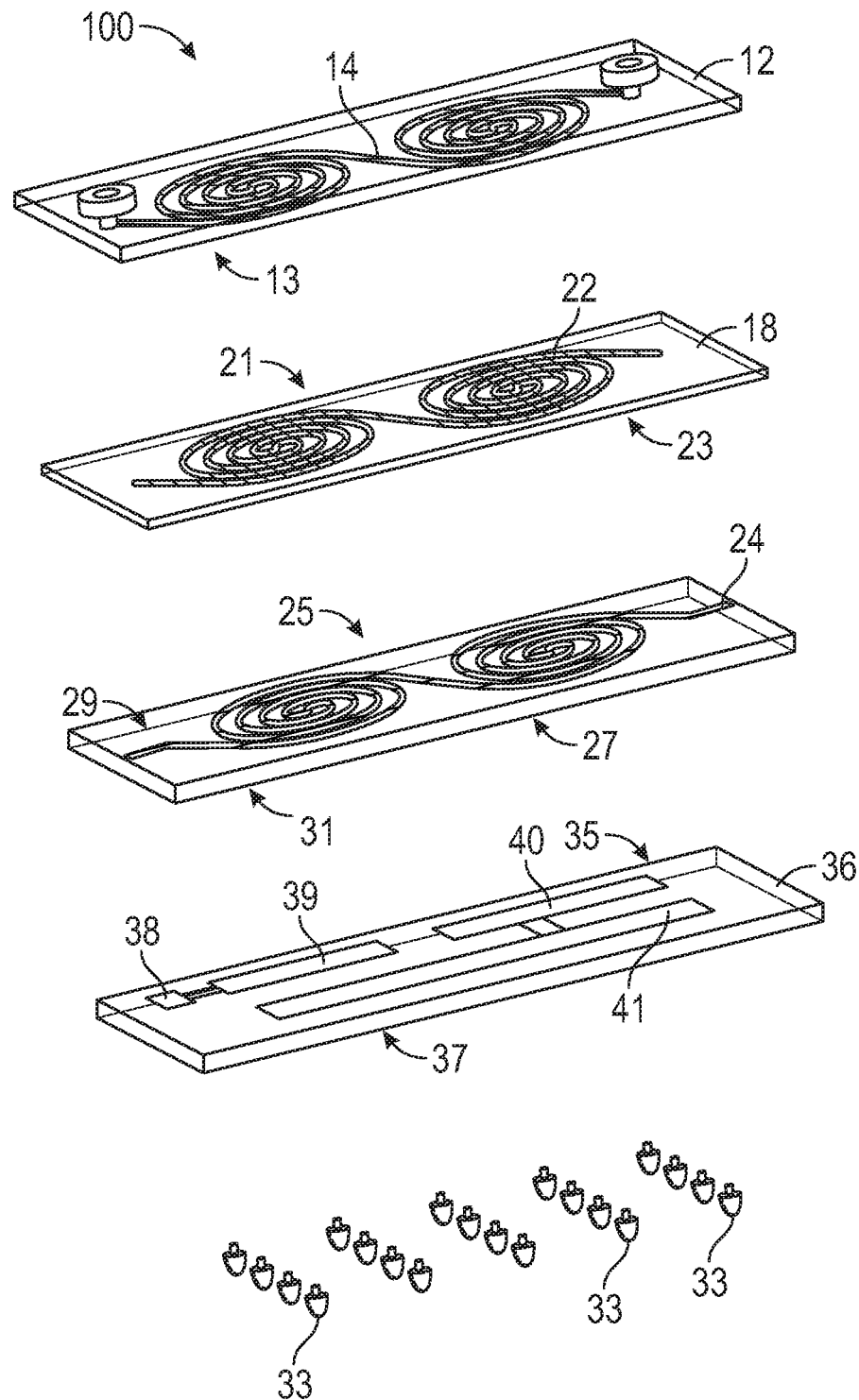
FIG. 28 shows an exploded side perspective view of another diagnostic assembly.
Figure 29:
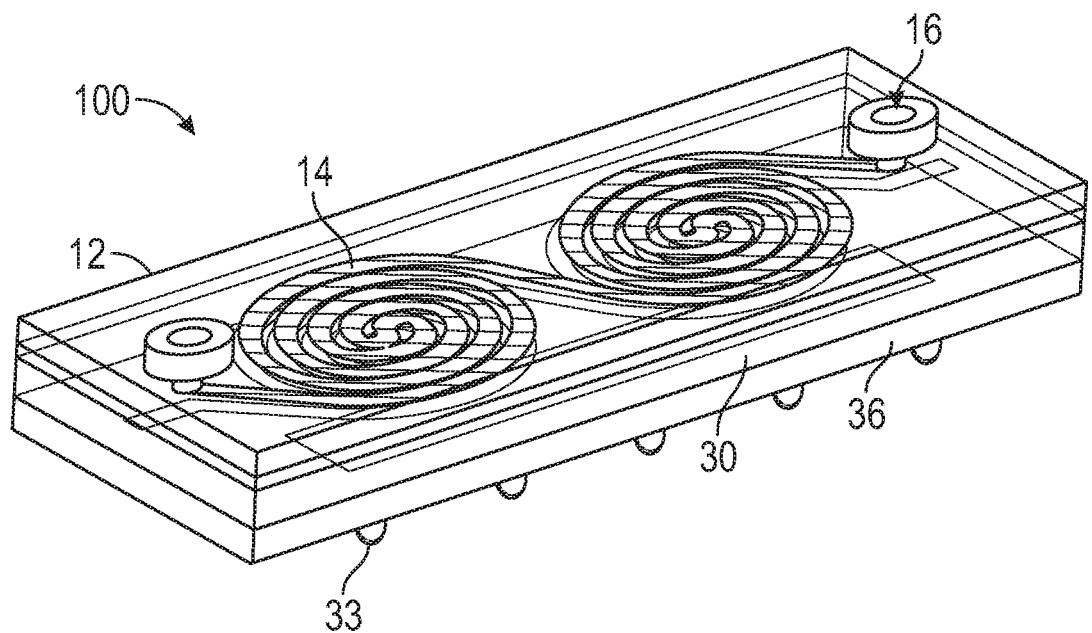
FIG. 29 shows an assembled side perspective view of the assembly of FIG. 28.

In another embodiment and as shown in FIGS. 28 and 29, diagnostic assembly 100 includes channel layer 12 having channel 14, insulation layer 18 having coating 22, circuit layer 24 fabricated on base member 30, control panel layer 36 and a layer of lights 33.

Figure 33:
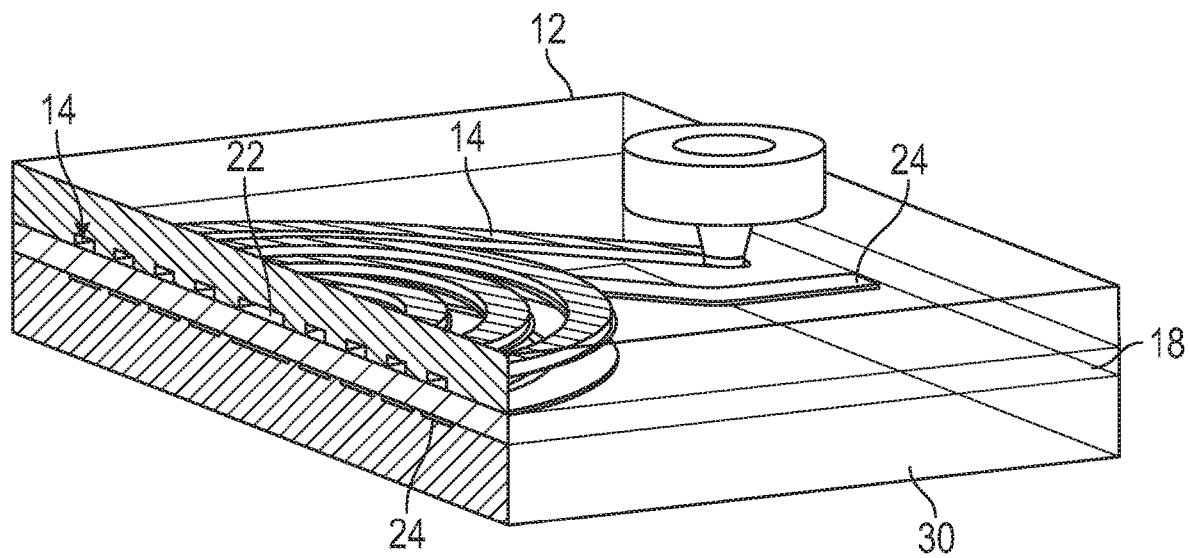
FIG. 33 shows a partial cross-sectional side view of the assembly of FIG. 29.

During fabrication of diagnostic assembly 100 (FIG. 28) and similar to assembly 10, the bottom surface 13 of channel layer 12 is mounted to the top surface 21 of substrate/insulation layer 18 to seal the bottom surface 13 of the channel layer 12, with the coating 22 being positioned under the channel 14. As such, the insulation layer 18 covers the bottom surface 13 of the channel layer 12, thereby closing and sealing the open channel 14 on the bottom surface 13. See also FIG. 33.

The cancer antibodies of coating 22 are attached to the insulation layer 18 in order to facilitate the antigen and antibody bonding during operation of assembly 100. In exemplary embodiments, the antibody coating 22 is placed at the locations where the micro-channel 14 interacts with the insulation layer 18 (e.g., coating 22 takes a shape/form that substantially matches the shape/form of channel 14, with the coating 22 positioned underneath channel 14). As the mounted insulation layer 18 is the bottom surface of channel 14, when blood flows in and through channel 14, the antigens of cancer in the blood will react with antibodies of coating 22. Insulation layer 18 can include material that is highly thermally conductive and that electrically insulates.

Figure 30:
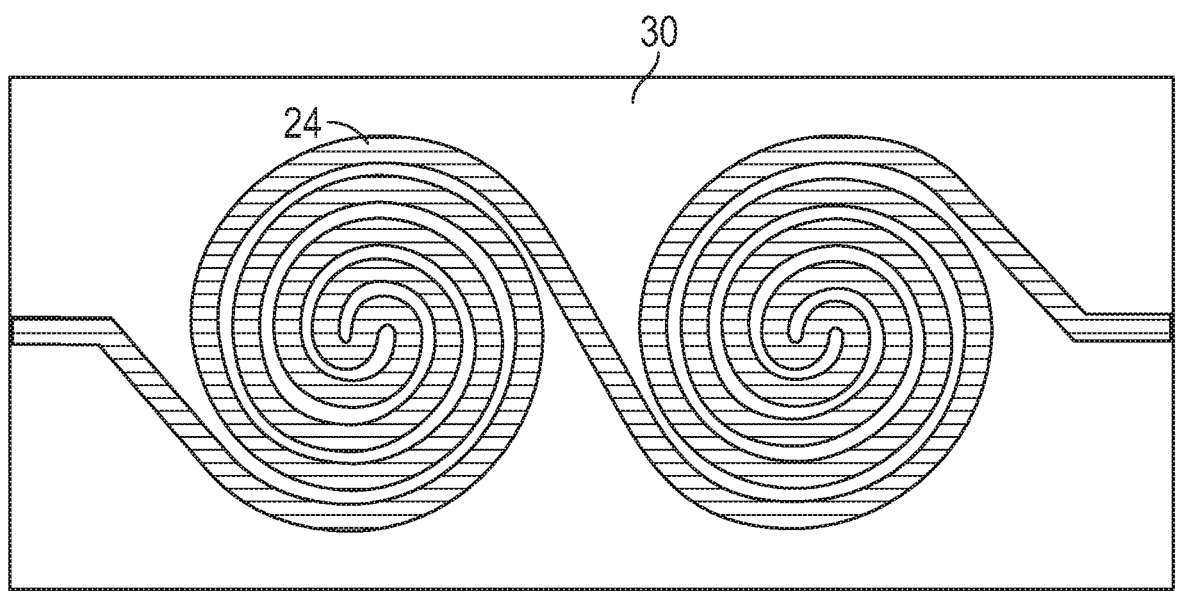
FIG. 30 shows a top view of an exemplary circuit layer.
Figure 31:
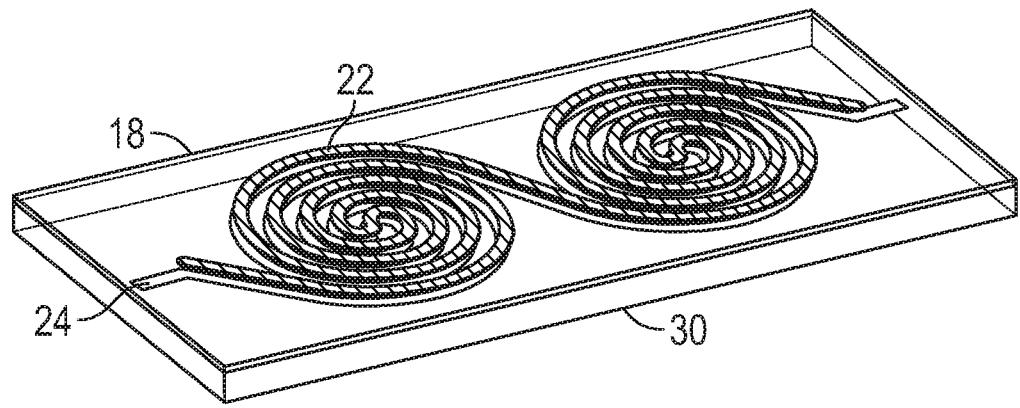
FIG. 31 shows a side perspective view of the circuit layer of FIG. 30, with circuit layer covered by an insulating layer.
Figure 32:
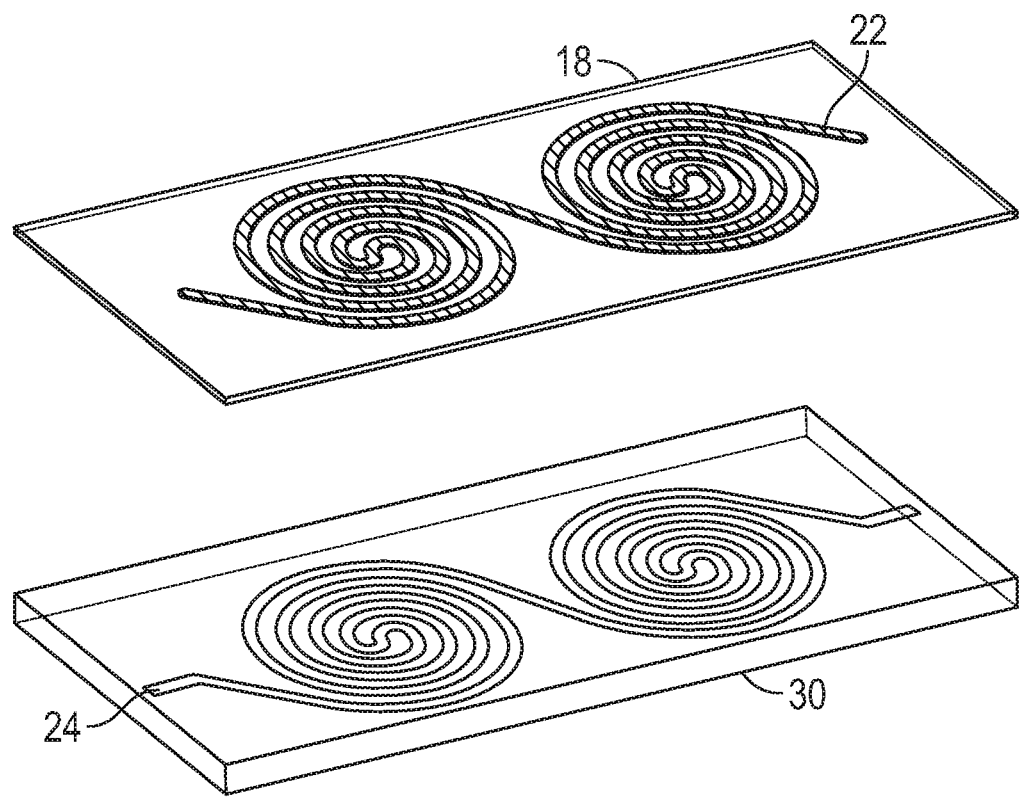
FIG. 32 shows an exploded side perspective view of the layers of FIG. 31.

FIGS. 10 and 30 are top views of an exemplary circuit layer 24, with the circuit layer 24 including a top surface 25 and a bottom surface 27, and with the circuit layer 24 fabricated on a top surface 29 of base member 30 (e.g., polymeric base member 30) (FIGS. 28 and 30). Exemplary circuit layer 24 takes the form of a substantially spiral-shaped layer 24 that substantially matches the spiral shape of channel 14 and/or coating 22. It is noted that circuit layer 24 can include self-insulating material or the like.

During fabrication of diagnostic assembly 100 (FIG. 28), the bottom surface 23 of insulation layer 18 is mounted to the top surface 25 of circuit layer 24 and to the top surface 29 of base member 30, with the circuit layer 24 being positioned under the coating 22.

The bottom surface 31 of base member 30 is mounted to the top surface 35 of control panel layer 36. The bottom surface 37 of control panel layer 36 includes a plurality of lights (e.g., LED lights 33) mounted thereon.

Figure 35:
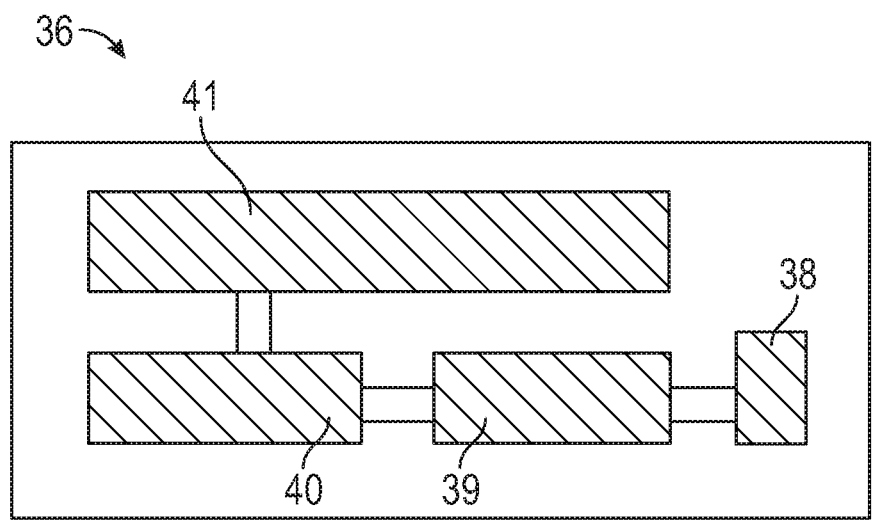
FIG. 35 shows a top view of another exemplary control panel layer.
Figure 36:
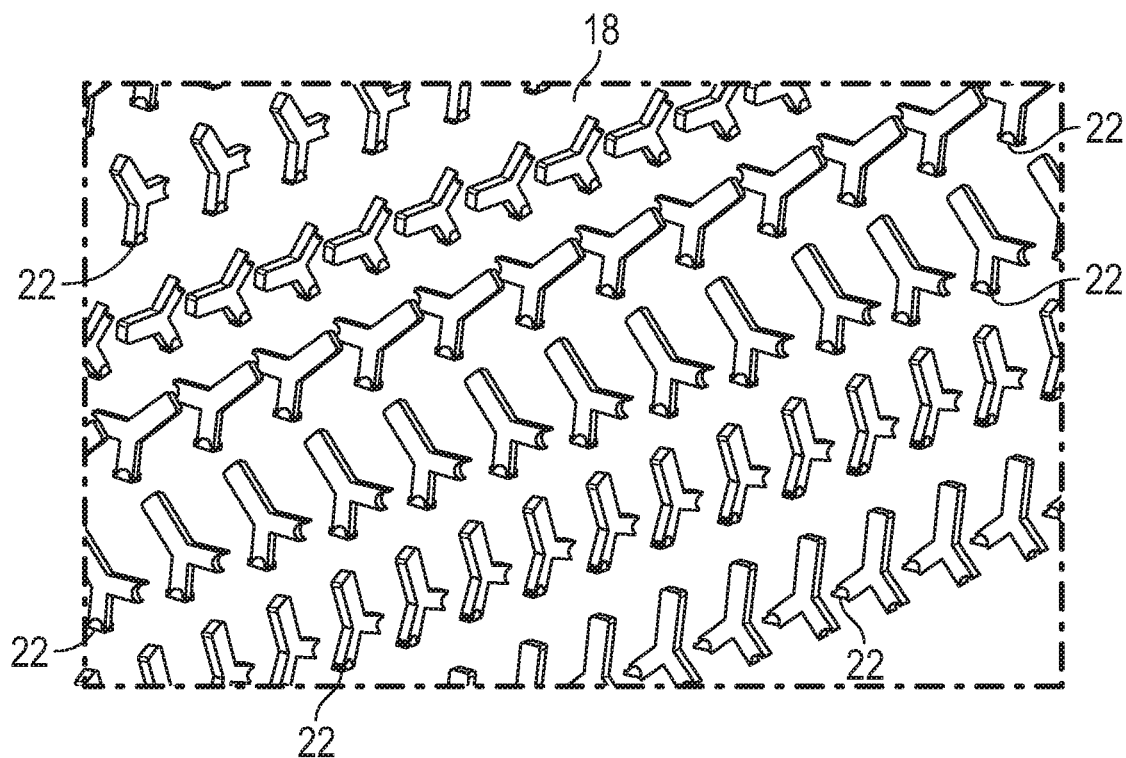
FIG. 36 shows the surface of the insulating layer with the antibodies coated and antigens attached to corresponding antibodies.
Figure 37:
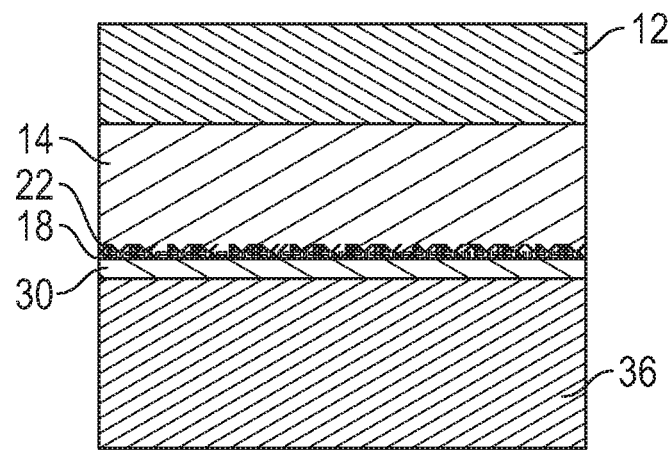
FIGS. 37-38 are partial cross-sectional views of the assembly of FIG. 29.
Figure 38:
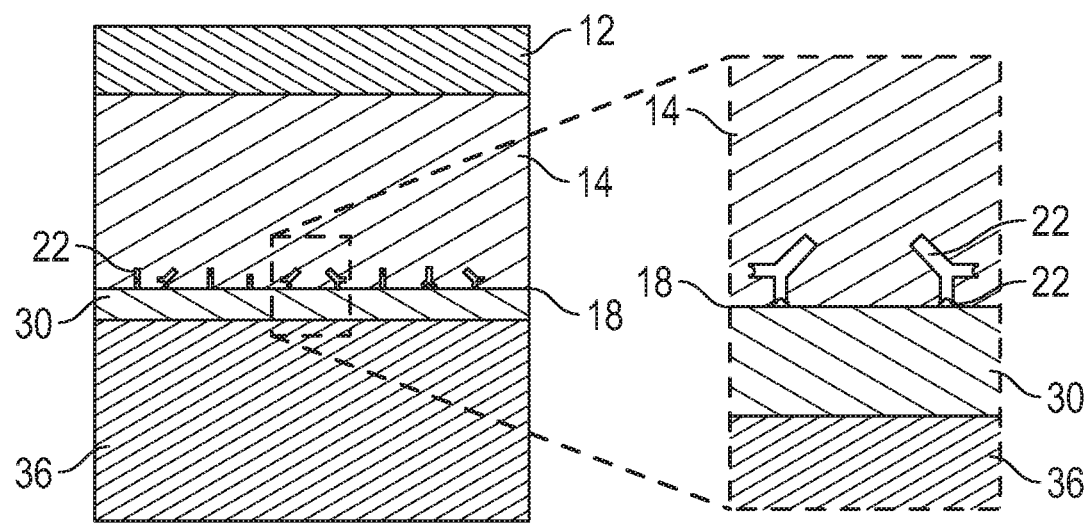

As shown in FIG. 35, control panel layer 36 includes an electrical oscillation generator 38, a frequency signal receiver 39, a signal amplifier 40 and a signal processor 41. As such, control panel layer 36 is configured to generate an electrical oscillation signal (input) via generator 38 and a frequency receiving signal (output) via receiver 39, and the signal amplifier 40 and signal processor 41 are configured to switch on the LED lights 33 to show the diagnosis results. Stated another way, control panel layer 36 includes various electrical processing units such as electrical oscillation generator 38, frequency signal receiver 39, signal amplifier 40 and signal processor 41 for sensing the disease with frequency response variation to electrical oscillation in channel 14.

The layer of LED lights 33 can be used to indicate the diagnosis of the disease both quantitatively and qualitatively. The lighting of these lights 33 can depend on the diagnosis results. In general, the lights 33 are set in patterns and evenly distributed across surface 37.

More particularly and with respect to diagnostic assembly 100, the detection of antigens in the blood sample can be determined using the dynamic capacitance method. The frequency output to the circuit layer 24 is varied with the bonding of antigen and antibody on it. The variation frequency of electrical oscillation between input and output of the circuit layer 24 gives the indication of antigen and antibody interaction at its surface. As the electric pulse is more precise compared to an acoustic wave, even the minor variations in the wave frequency can be identified. The formation of antigen-antibody complexes can be identified, with the change in frequency response to the continuous input electric oscillation frequency. So once the existence of antigens in the blood sample is established, the disease related to a specific antigen can be diagnosed.

The paratope of antibody, and epitope of antigen do have high specificity so that the interaction of antigen and antibody do happen only with the corresponding one. So in the pool of antibodies and antigens the interactions occur only between the antibody only with that specific antigen. So identifying the specific antigen in the blood sample will diagnose the existence of that specific disease antigen in blood, which ultimately confirms the existence of that specific disease in blood.

In the dynamic capacitance model of assembly 100, the change in the mass will impact the frequency response of electrical oscillation. When the bonding of antigen and antibody occur the change in mass impacts the output response of the frequency generated. The input is electric oscillation generated with an electric pulse. As noted above, the circuit layer 24 is fabricated/positioned at the bottom part of the channel 14.

In exemplary embodiments, the circuit layer 24 is designed similar to the shape of the micro channel 14 and aligned against the bottom of the PDMS mold/layer 12 (with thin layer 18 positioned therebetween), so that once layer 24 attaches, layer 24 helps to form the channel 14 (e.g., in the rectangular channel 14, three sides will be PDMS mold/layer 12 and one side is closed by circuit layer 24 (with thin layer 18 positioned over layer 24).

As noted, the circuit layer 24 can have some insulation (e.g., layer 18) as it should not have direct contact with the blood flow (since blood is an electrical conductor). So the circuit layer 24 is coated with layer 18 (e.g., a thin film/layer 18 of electrically insulated material whose thickness is of single order microns). The antibodies are plotted/coated just above this layer 18. So when the blood flows through this channel 14, if there are any antigens, they will form antigen and antibody complexes over the circuit layer 24.

The circuit layer 24 will be continuously provided with electrical oscillation from the electric oscillation generator 38. But there will be change in the frequency output, whenever the antigen-antibody interaction takes place. This output signal from circuit layer 24 is taken to the frequency receiver 39. Therefore, the circuit layer 24 is also in direct contact with this receiver 39.

The control panel layer 36 is well designed with the nano scale electrical oscillation generator 38 (impulse) which has direct contact with the circuit layer 24. So when the electrical oscillation is continously being sent, there will be a change in the receiving signal (by frequency signal receiver 39), when the antigens from the blood sample form complexes with antibodies (coated on the surface of the circuit layer 24). These variations in the frequency response confirms the bonding of antigen and antibody. Once the signal is received, it goes through an enhancement due to the amplifier 40. This amplified signal is then sent to the signal processor/voltage converter 41, where the received signal is matched to the permissible limits and if it is not fit to the acceptable limits, the result will be carried to the LED lights 33 in the form of voltage.

Thus, the indication of the lights 33 gives one the confirmation of the existence of antigens in the blood sample. So thus the diagnosis process is carried out using the variation of frequency from electric oscillation.

Figure 34:
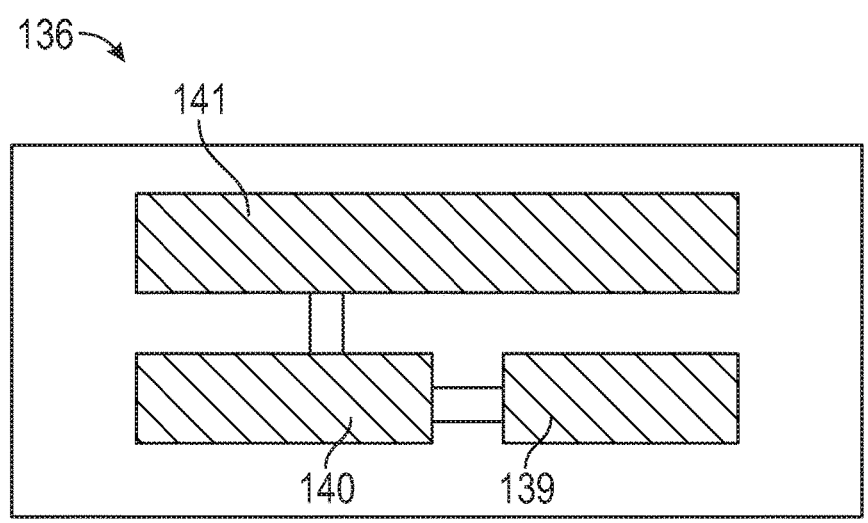
FIG. 34 shows a top view of an exemplary control panel layer.

In another embodiment and as shown in FIG. 34, diagnostic assembly 100 can utilize control panel layer 136 in lieu of control panel layer 36. Control panel layer 136 includes signal receiver 139, a signal amplifier 140 and a signal processor 141. As such, control panel layer 136 is configured to process/receive a signal via signal receiver 139 and amplifier 140, and signal processor 141 is configured to process the signal (output) and switch on the LED lights 33 to show the diagnosis results. Stated another way, control panel layer 136 includes various processing units such as signal receiver 139, signal amplifier 140 and signal processor 141 for sensing/diagnosing the disease with temperature variations in channel 14. As such, after a fluid flow (e.g., blood) is introduced to the channel 14, the circuit layer 24 can be configured to generate signals based on interactions of the fluid flow with the coated area 22, and the control panel layer 136 can be configured to process and receive the signals via the signal receiver 139 and the signal amplifier 140, and the signal processor 141 can be configured to process the signals and to visually display (e.g., via lights 33) the signals (e.g., the circuit layer 24 can be configured to generate signals based on temperature or voltage variations in the channel 14; or be configured to generate signals based on frequency response variations to electrical oscillation in the channel 14 as discussed above).

Figure 39:
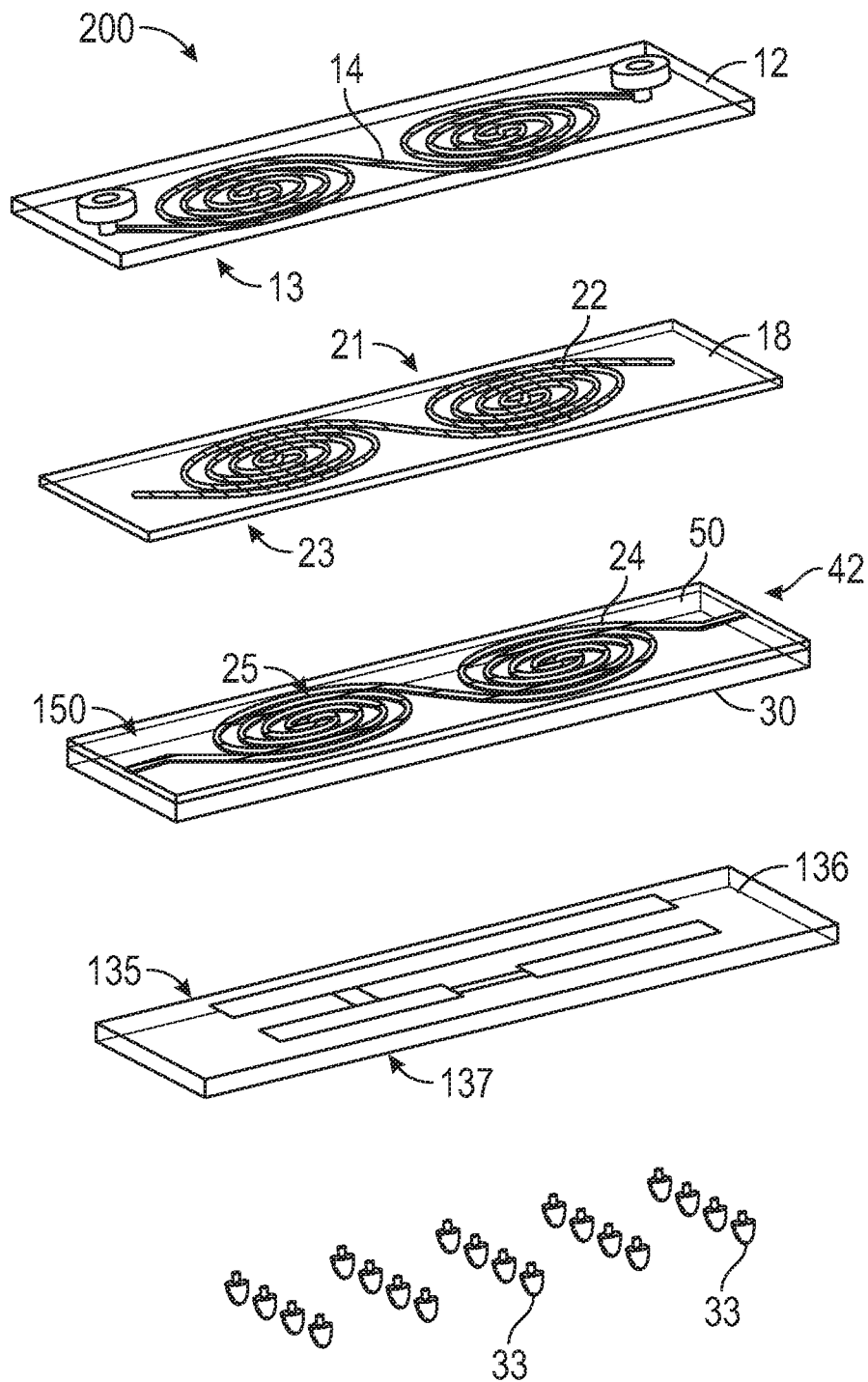
FIG. 39 shows an exploded side perspective view of another diagnostic assembly.
Figure 40:
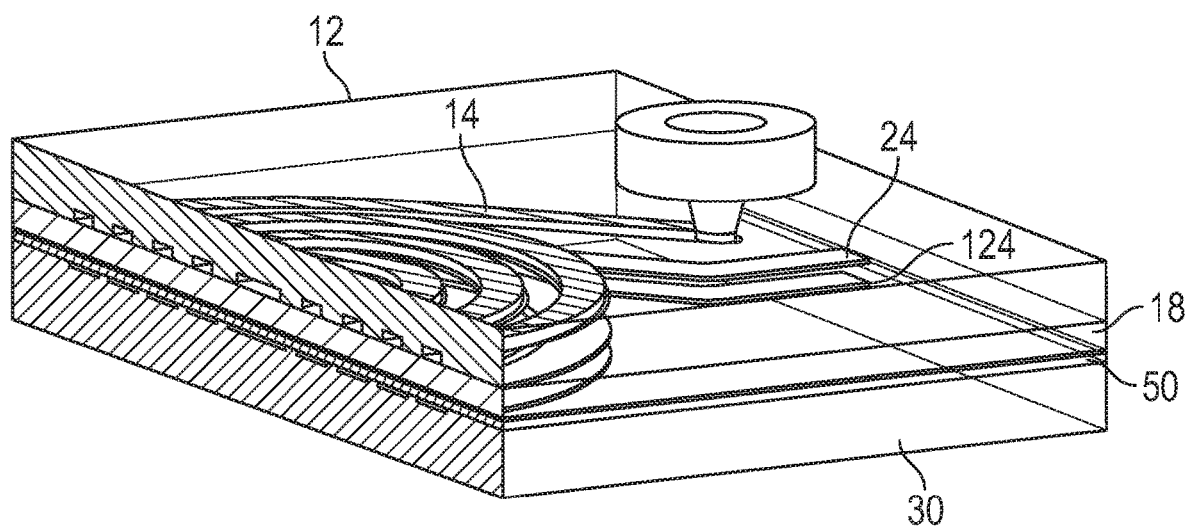
FIG. 40 shows a partial cross-sectional side view of the assembly of FIG. 39.

In another embodiment and as shown in FIGS. 39 and 40, diagnostic assembly 200 includes channel layer 12 having channel 14, insulation layer 18 having coating 22, dual circuit layer 42, control panel layer 136 and a layer of lights 33.

During fabrication of diagnostic assembly 200 (FIG. 39) and similar to assembly 10/100, the bottom surface 13 of channel layer 12 is mounted to the top surface 21 of insulation layer 18 to seal the bottom surface 13 of the channel layer 12, with the coating 22 being positioned under the channel 14. As such, the insulation layer 18 covers the bottom surface 13 of the channel layer 12, thereby closing and sealing the open channel 14 on the bottom surface 13. See also FIG. 40.

The cancer antibodies of coating 22 are attached to the insulation layer 18 in order to facilitate the antigen and antibody bonding during operation of assembly 200. The antibody coating 22 can be placed at the locations where the micro-channel 14 interacts with the insulation layer 18 (e.g., coating 22 takes a shape/form that substantially matches the shape/form of channel 14, with the coating 22 positioned underneath channel 14). As the mounted insulation layer 18 is the bottom surface of channel 14, when blood flows in and through channel 14, the antigens of cancer in the blood will react with antibodies of coating 22. Insulation layer 18 can include material that is highly thermally conductive and that electrically insulates.

Figure 41:
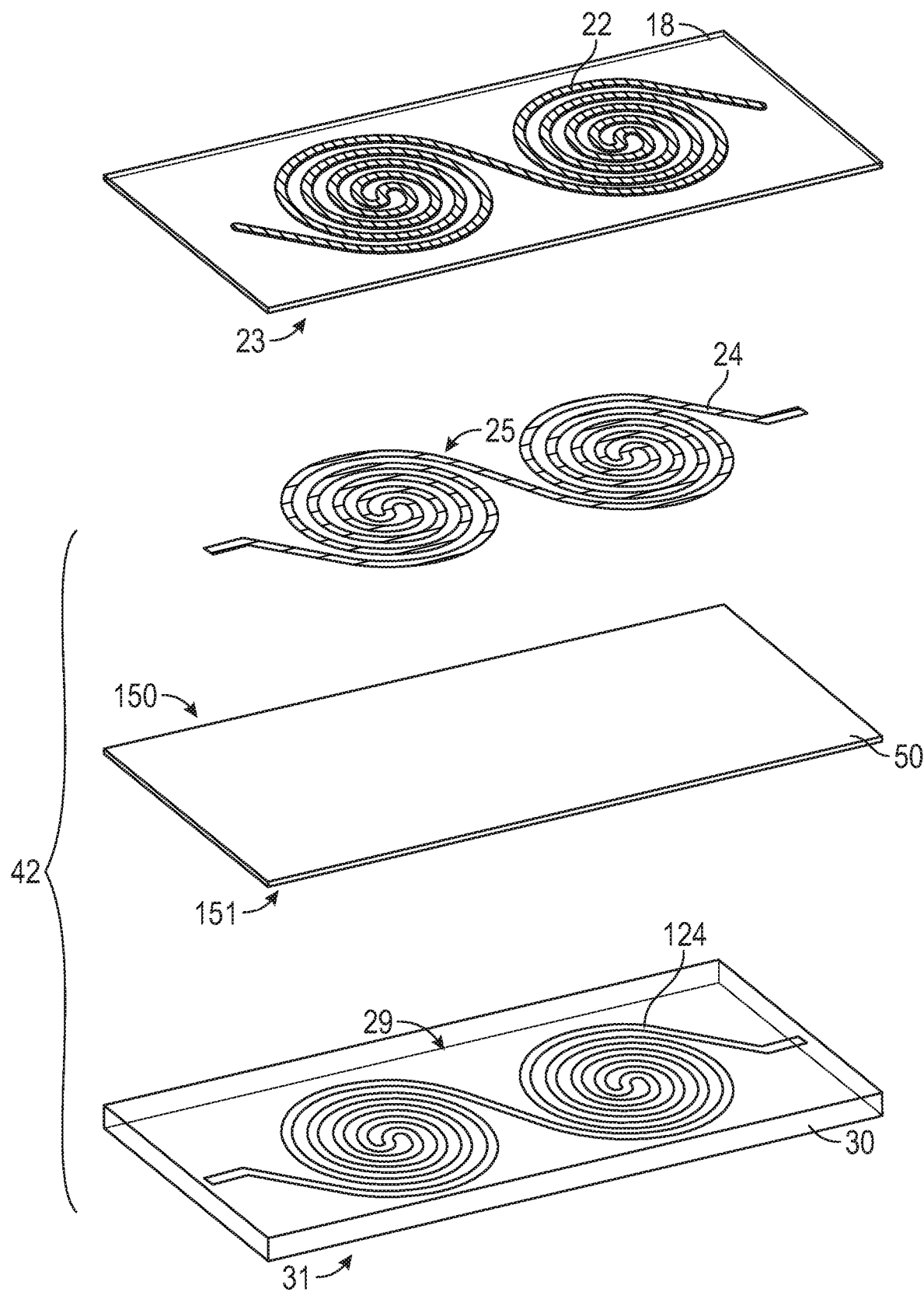
FIG. 41 is an exploded view of an exemplary dual circuit layer and insulation layer.
Figure 42:
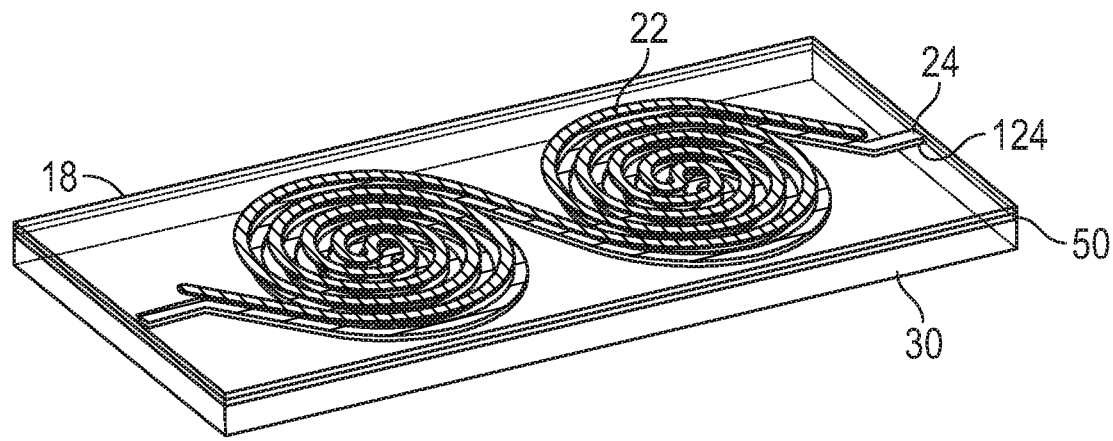
FIG. 42 is an assembled view of the layers of FIG. 41.

FIG. 41 is an exploded side view of an exemplary dual circuit layer 42. Dual circuit layer 42 includes a first circuit layer 24 (e.g., capacitor 24) positioned/mounted on a dielectric material 50, and with the dielectric material 50 positioned/mounted on a second circuit layer 124 (e.g., capacitor 24). Second circuit layer 124 can be fabricated on a base member 30.

Exemplary circuit layers 24, 124 take the form a substantially spiral-shaped layer 24, 124 that substantially matches the spiral shape of channel 14 and/or coating 22.

During fabrication of diagnostic assembly 200, the bottom surface 23 of insulation layer 18 is mounted to the top surface 25 of circuit layer 24 and to the top surface 150 of dielectric member 50, with the circuit layer 24 being positioned under the coating 22.

The bottom surface 151 of member 50 (FIG. 41) is mounted to circuit layer 124 and to the top surface 29 of member 30. The bottom surface 31 of base member 30 is mounted to the top surface 135 of control panel layer 136 (FIGS. 39 and 41). The bottom surface 137 of control panel layer 136 includes a plurality of lights (e.g., LED lights 33) mounted thereon.

Control panel layer 136 includes signal receiver 139, a signal amplifier 140 and a signal processor 141. As such, control panel layer 136 is configured to process/receive a signal via signal receiver 139 and amplifier 140, and signal processor 141 is configured to process the signal (output) and switch on the LED lights 33 to show the diagnosis results. Stated another way, control panel layer 136 includes various processing units such as signal receiver 139, signal amplifier 140 and signal processor 141 for sensing/diagnosing the disease with variations of voltage (or with frequency response variations or temperature variations) in channel 14 (e.g., via a capacitance sensing method).

The layer of LED lights 33 can be used to indicate the diagnosis of the disease both quantitatively and qualitatively. The lighting of these lights 33 can depend on the diagnosis results. In general, the lights 33 are set in patterns and evenly distributed across surface 137.

It is also noted that assembly 200 could utilize control panel layer 36 in lieu of layer 136.

Although the systems and methods of the present disclosure have been described with reference to exemplary embodiments thereof, the present disclosure is not limited to such exemplary embodiments and/or implementations. Rather, the systems and methods of the present disclosure are susceptible to many implementations and applications, as will be readily apparent to persons skilled in the art from the disclosure hereof. The present disclosure expressly encompasses such modifications, enhancements and/or variations of the disclosed embodiments. Since many changes could be made in the above construction and many widely different embodiments of this disclosure could be made without departing from the scope thereof, it is intended that all matter contained in the drawings and specification shall be interpreted as illustrative and not in a limiting sense. Additional modifications, changes, and substitutions are intended in the foregoing disclosure. Accordingly, it is appropriate that the appended claims be construed broadly and in a manner consistent with the scope of the disclosure.

What is claimed is:

1. A diagnostic assembly comprising:
    a channel layer having a top surface and a bottom surface, the channel layer including a channel that extends from the bottom surface toward the top surface, with the channel ending at a point between the top and bottom surfaces;
    an insulation layer having a top surface and a bottom surface, the top surface of the insulation layer having a coated area, with the top surface of the insulation layer positioned under the bottom surface of the channel layer to seal the channel, with the coated area positioned under the channel;
    a circuit layer having a top surface and a bottom surface, the top surface of the circuit layer positioned under the bottom surface of the insulation layer and under the coated area;
    wherein after a fluid flow is introduced to the channel, the circuit layer is configured to generate signals based on interactions of the fluid flow with the coated area.

2. The assembly of claim 1, wherein the channel layer includes polydimethylsiloxane;
    wherein the channel includes a shape selected from the group consisting of serpentine, spiral, straight and curved; and
    wherein the channel is hydrophilic.

3. The assembly of claim 1, wherein the channel includes a width from about 200 μm to about 300 μm and includes a depth from about 60 μm to about 100 μm.

4. The assembly of claim 1, wherein the fluid flow includes blood and the coated area includes antibodies or antigens; and
    wherein the channel extends from an inlet well to an outlet well.

5. The assembly of claim 1, wherein the shape of the coated area substantially matches the shape of the channel; and
    wherein the shape of the circuit layer substantially matches the shape of the channel.

6. The assembly of claim 1, wherein the circuit layer is mounted to a polymeric base member, the polymeric base member having a plurality of lights mounted thereto, the plurality of lights configured to illuminate to display the signals.

7. A diagnostic assembly comprising:
    a channel layer having a top surface and a bottom surface, the channel layer including a channel that extends from the bottom surface toward the top surface, with the channel ending at a point between the top and bottom surfaces;
    an insulation layer having a top surface and a bottom surface, the top surface of the insulation layer having a coated area, with the top surface of the insulation layer positioned under the bottom surface of the channel layer to seal the channel, with the coated area positioned under the channel;
    a circuit layer having a top surface and a bottom surface, the top surface of the circuit layer positioned under the bottom surface of the insulation layer and under the coated area;
    a control panel layer mounted to the bottom surface of the circuit layer, the control panel layer including a signal receiver, a signal amplifier and a signal processor;
    wherein after a fluid flow is introduced to the channel, the circuit layer is configured to generate signals based on interactions of the fluid flow with the coated area;
    wherein the control panel layer is configured to process and receive the signals via the signal receiver and the signal amplifier, and the signal processor is configured to process the signals and to visually display the signals.

8. The assembly of claim 7 further comprising a plurality of lights mounted to the control panel layer, the plurality of lights configured to illuminate to display the signals.

9. The assembly of claim 7, wherein the control panel layer further includes an electrical oscillation generator; and
    wherein the circuit layer is configured to generate signals based on frequency response variations to electrical oscillation from the channel.

10. The assembly of claim 7, wherein the circuit layer is configured to generate signals based on temperature variations in the channel.

11. The assembly of claim 7, wherein the channel has a cross-sectional shape selected from the group consisting of rectangular, square, eclipse-shaped, circular, rhombus, trapezoid and polygonal.

12. The assembly of claim 7, wherein the fluid flow includes blood and the coated area includes antibodies or antigens; and
wherein the channel extends from an inlet well to an outlet well.

13. The assembly of claim 7, wherein the shape of the coated area substantially matches the shape of the channel; and
wherein the shape of the circuit layer substantially matches the shape of the channel.

14. A diagnostic assembly comprising:
a channel layer having a top surface and a bottom surface, the channel layer including a channel that extends from the bottom surface toward the top surface, with the channel ending at a point between the top and bottom surfaces;
an insulation layer having a top surface and a bottom surface, the top surface of the insulation layer having a coated area, with the top surface of the insulation layer positioned under the bottom surface of the channel layer to seal the channel, with the coated area positioned under the channel;
a first circuit layer and a second circuit layer, with a dielectric material positioned between the first and second circuit layers, a top surface of the first circuit layer positioned under the bottom surface of the insulation layer and under the coated area, and a bottom surface of the second circuit layer mounted to a base member;
a control panel layer mounted to a bottom surface of the base member, the control panel layer including a signal receiver, a signal amplifier and a signal processor;
wherein after a fluid flow is introduced to the channel, the first and second circuit layers are configured to generate signals based on interactions of the fluid flow with the coated area.

15. The assembly of claim 14, wherein the control panel layer is configured to process and receive the signals via the signal receiver and the signal amplifier, and the signal processor is configured to process the signals and to visually display the signals.

16. The assembly of claim 14, further comprising a plurality of lights mounted to the control panel layer, the plurality of lights configured to illuminate to display the signals.

17. The assembly of claim 14, wherein the first and second circuit layers are configured to generate signals based on voltage variations in the channel.

18. The assembly of claim 14, wherein the channel layer includes polydimethylsiloxane;
wherein the channel includes a shape selected from the group consisting of serpentine, spiral, straight and curved;
wherein the channel is hydrophilic; and
wherein the channel has a cross-sectional shape selected from the group consisting of rectangular, square, eclipse-shaped, circular, rhombus, trapezoid and polygonal.

19. The assembly of claim 14, wherein the fluid flow includes blood and the coated area includes antibodies or antigens; and
wherein the channel extends from an inlet well to an outlet well.

20. The assembly of claim 14, wherein the shape of the coated area substantially matches the shape of the channel; and
wherein the shapes of the first and second circuit layers substantially match the shape of the channel.

* * * * *